(12) United States Patent
Biggs et al.

(10) Patent No.: US 6,599,311 B1
(45) Date of Patent: Jul. 29, 2003

(54) METHOD AND ASSEMBLY FOR LUNG VOLUME REDUCTION

(75) Inventors: Michael Biggs, San Francisco, CA (US); Bryan Loomas, Los Gatos, CA (US); Steven Masterson, San Francisco, CA (US); Keith M. Burger, San Francisco, CA (US); Dave Haugaard, San Jose, CA (US); James M. Davenport, Fallbrook, CA (US); John Arthur Ross, Tracy, CA (US)

(73) Assignee: Broncus Technologies, Inc., Mountain View, CA (US)

( * ) Notice: Subject to any disclaimer, the term of this patent is extended or adjusted under 35 U.S.C. 154(b) by 0 days.

(21) Appl. No.: 09/576,786

(22) Filed: May 23, 2000

Related U.S. Application Data

(63) Continuation-in-part of application No. 09/092,727, filed on Jun. 5, 1998, now Pat. No. 6,174,323.

(51) Int. Cl.[7] .............................................. A61B 17/04
(52) U.S. Cl. ...................... 606/232; 606/144; 606/233; 128/898; 623/23.65
(58) Field of Search ................................ 606/232, 149, 606/104; 623/23.64, 23.65

(56) References Cited

U.S. PATENT DOCUMENTS

| | | | |
|---|---|---|---|
| 4,898,156 A | * 2/1990 | Gatturna et al. | 411/512 |
| 5,084,058 A | * 1/1992 | Li | 289/17 |
| 5,306,290 A | * 4/1994 | Martins et al. | 215/309 |
| 5,372,604 A | * 12/1994 | Trott | 411/922 |
| 5,478,353 A | 12/1995 | Yoon | |
| 5,507,754 A | 4/1996 | Green et al. | |
| 5,573,540 A | 11/1996 | Yoon | |
| 5,573,543 A | 11/1996 | Akopov et al. | |
| 5,749,899 A | 5/1998 | Bardin | |
| 5,752,965 A | * 5/1998 | Francis et al. | 227/178.1 |
| 5,810,848 A | 9/1998 | Hayhurst | |
| 5,827,298 A | 10/1998 | Hart et al. | |
| 5,865,791 A | 2/1999 | Whayne et al. | |
| 5,868,762 A | 2/1999 | Cragg et al. | |
| 5,908,429 A | 6/1999 | Yoon | |
| 5,957,953 A | 9/1999 | DiPoto et al. | |
| 5,972,022 A | 10/1999 | Huxel | |
| 5,984,917 A | 11/1999 | Fleischman | |
| 6,003,517 A | 12/1999 | Sheffield et al. | |
| 6,010,525 A | 1/2000 | Bonutti et al. | |

FOREIGN PATENT DOCUMENTS

| | | |
|---|---|---|
| EP | 0 643 945 A3 | 3/1995 |
| EP | 0 643 945 A2 | 3/1995 |
| WO | WO 96/40356 A1 | 12/1996 |

* cited by examiner

Primary Examiner—Gary Jackson
(74) Attorney, Agent, or Firm—Sanjay S. Bagade

(57) ABSTRACT

Methods and assemblies for reducing the volume of a lung. A plurality of anchors are anchored at different positions in the lung. A cord is attached to each of the anchors. The anchors are drawn towards one another via the cords to cause the lung to collapse, thus compressing the tissue in the lung and establishing a reduction in lung volume.

72 Claims, 25 Drawing Sheets

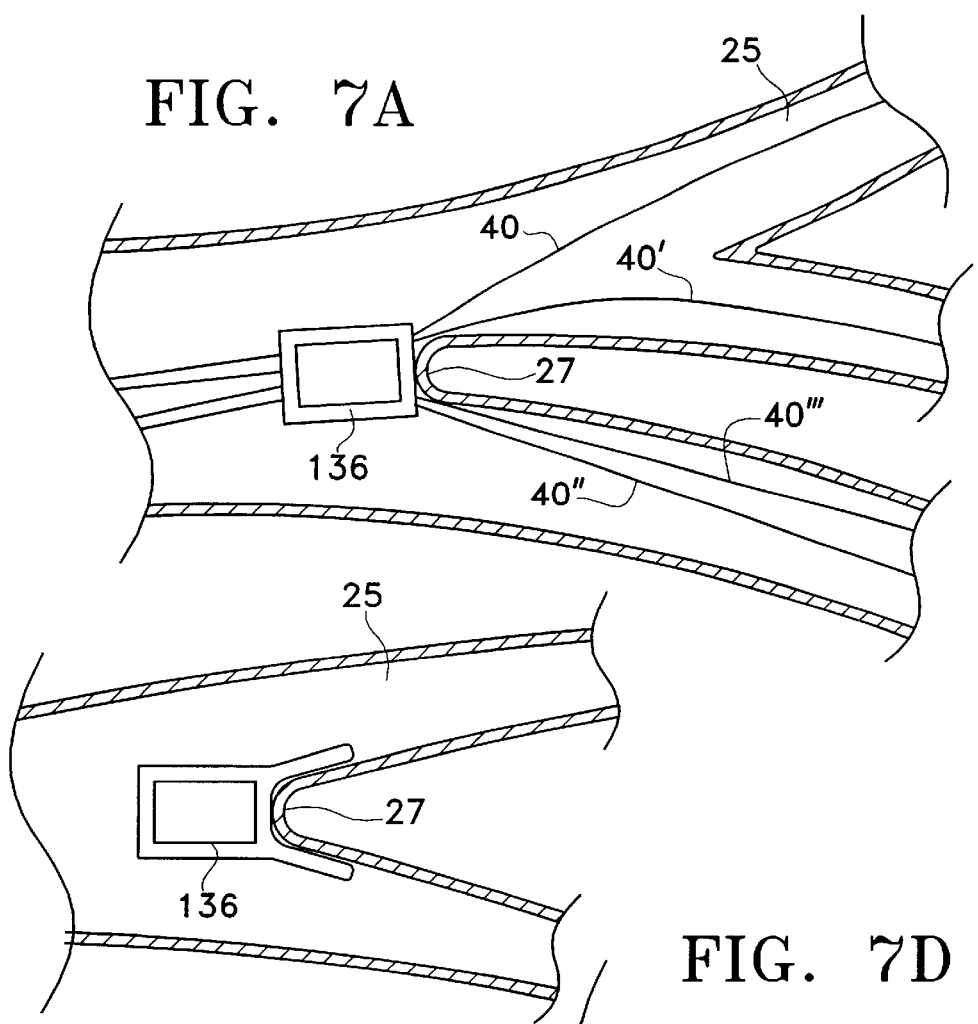
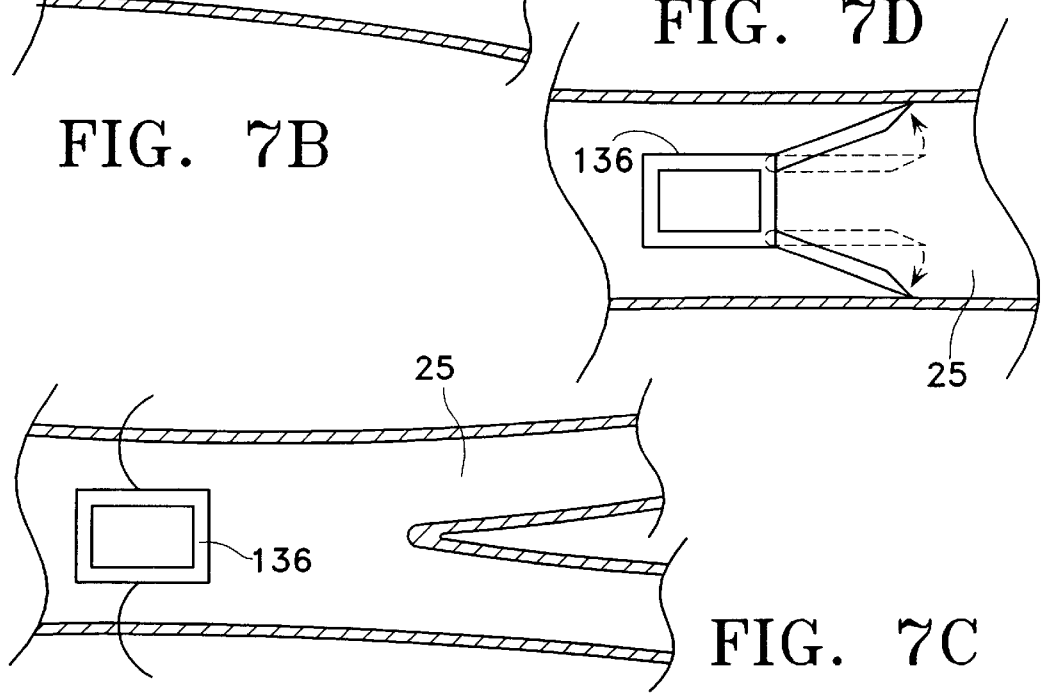
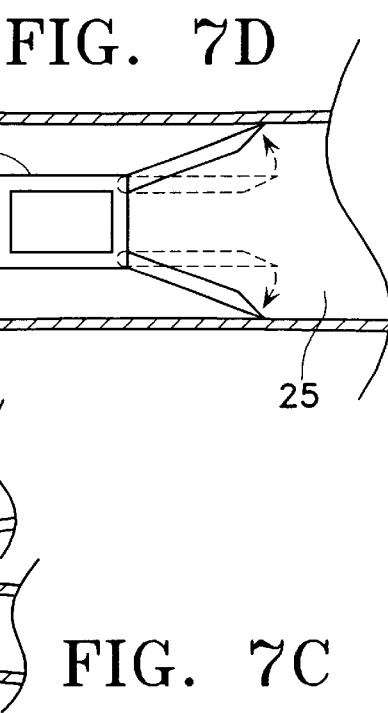

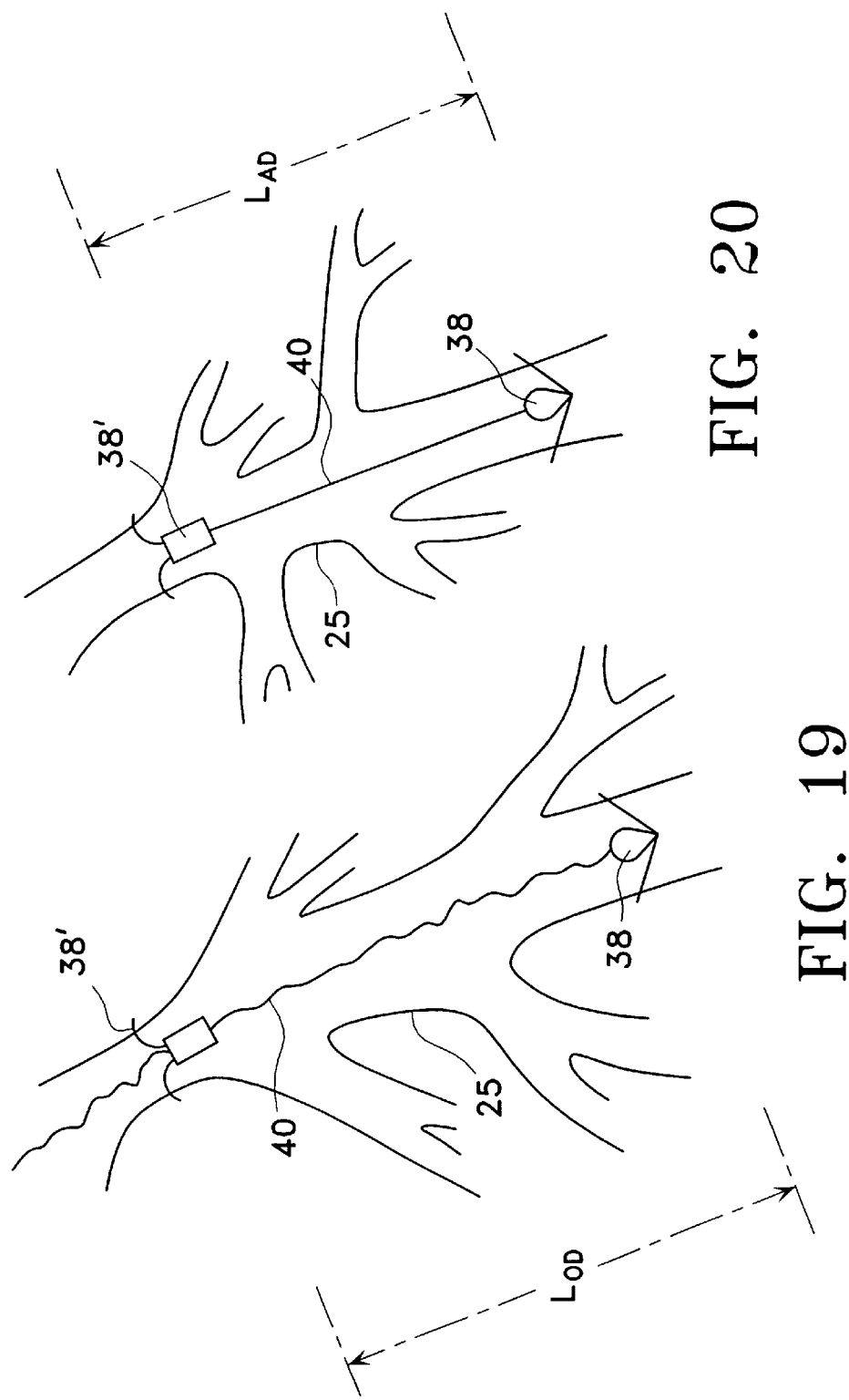

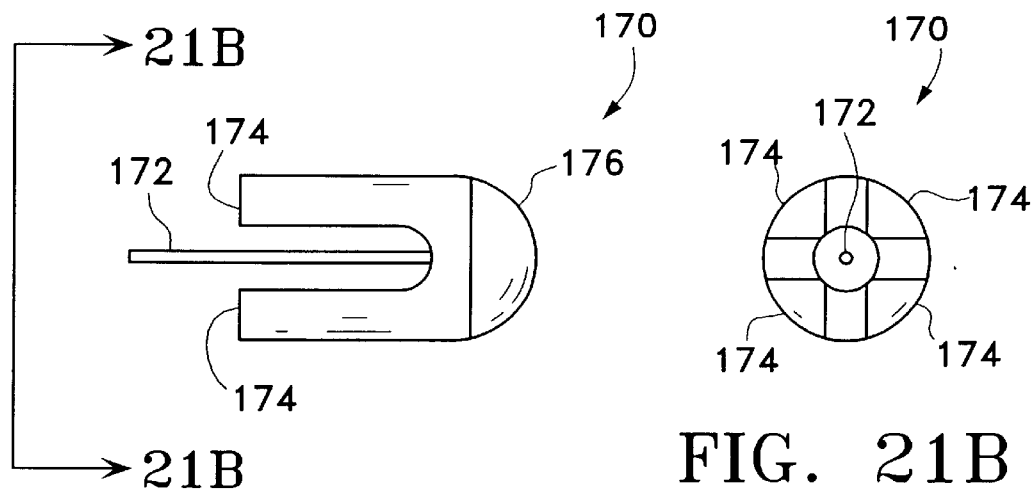
FIG. 21A
FIG. 21B
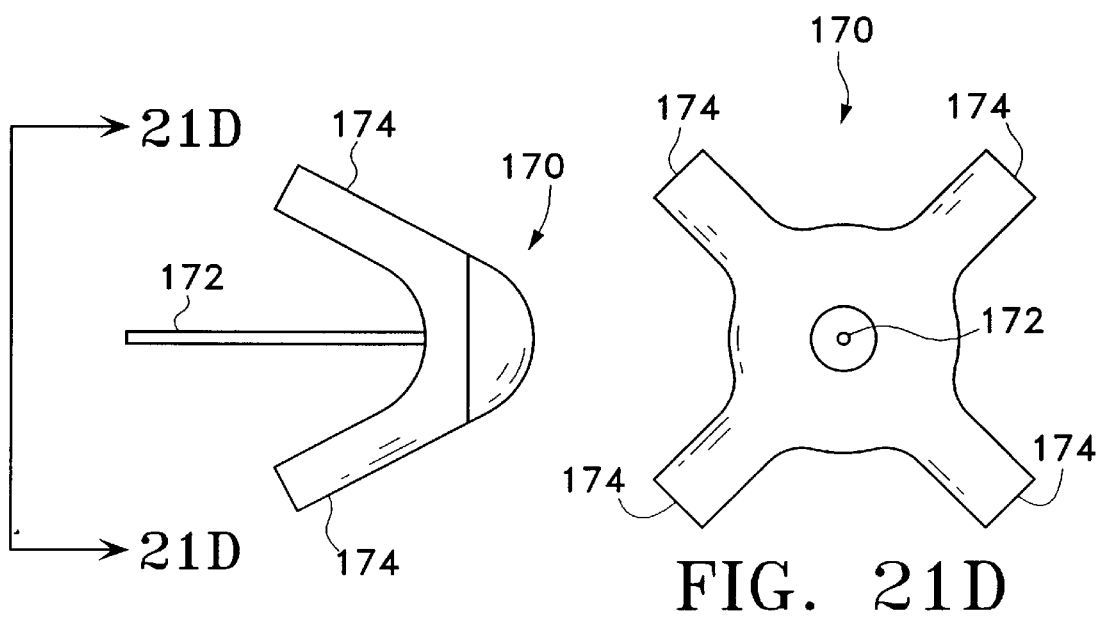
FIG. 21C
FIG. 21D

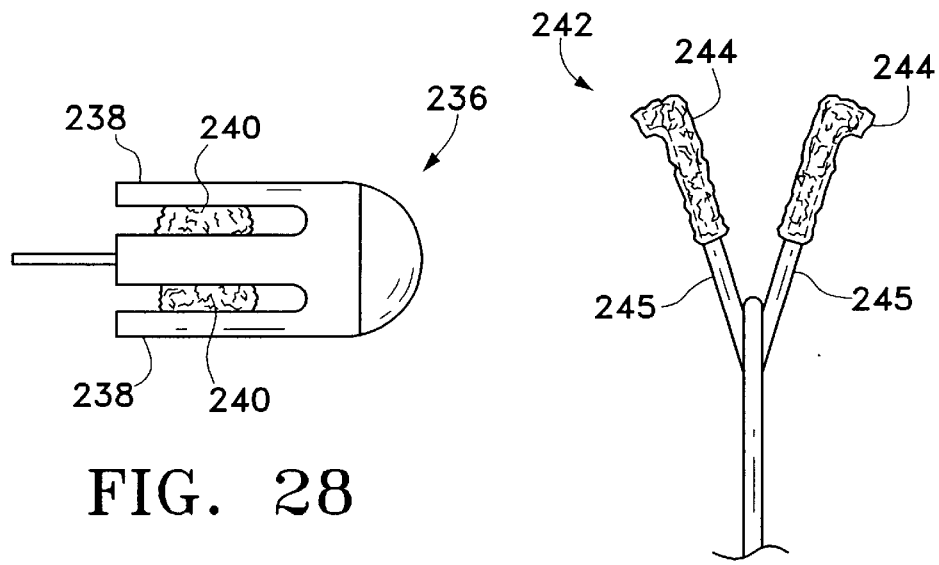
FIG. 28
FIG. 29
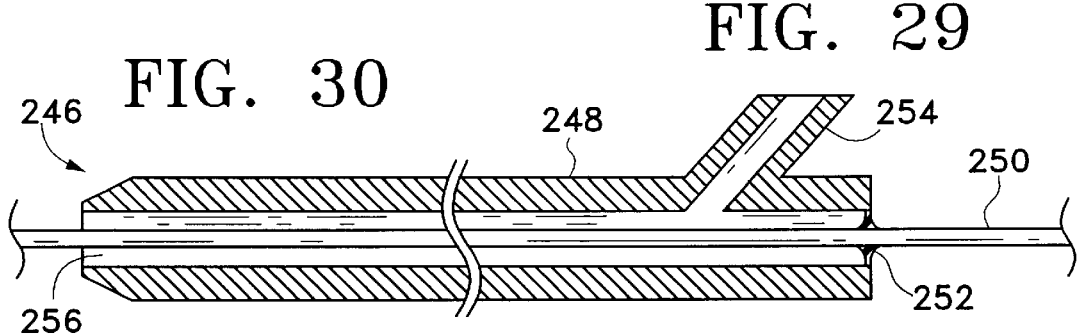
FIG. 30
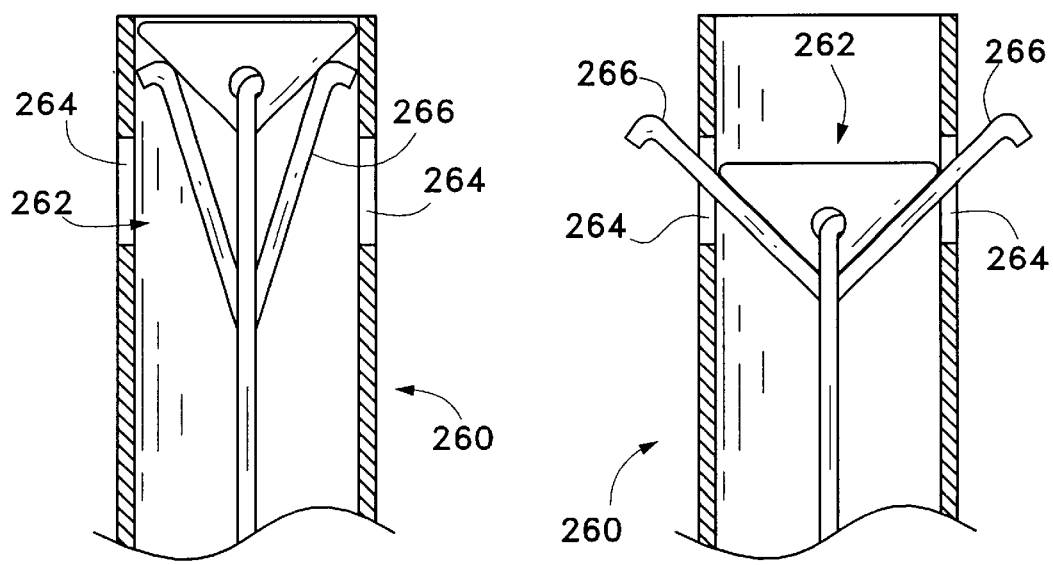
FIG. 31A
FIG. 31B

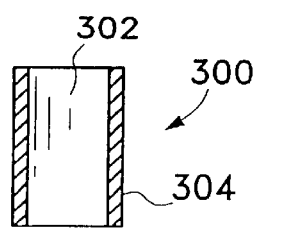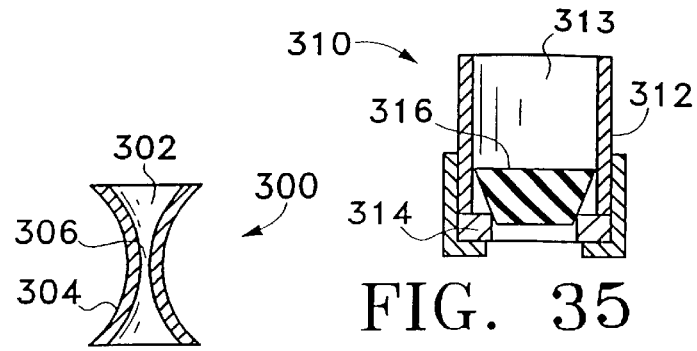
FIG. 34A    FIG. 34B    FIG. 35
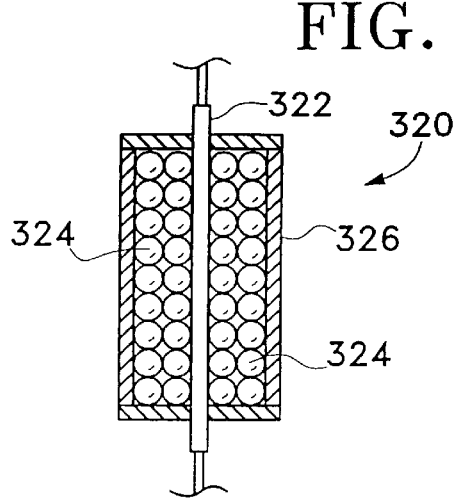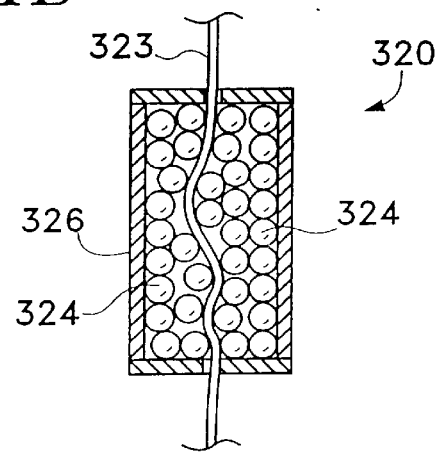
FIG. 36A    FIG. 36B
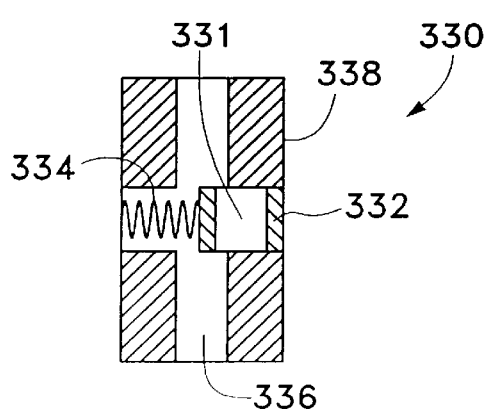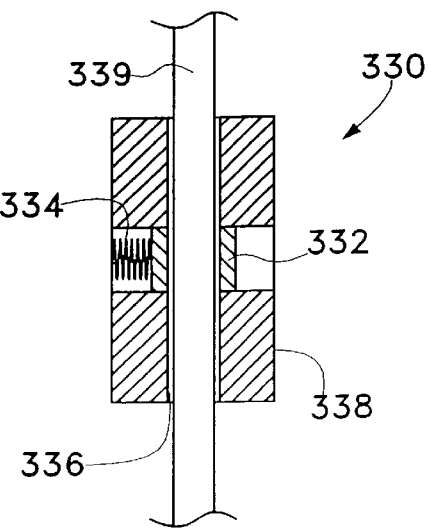
FIG. 37A    FIG. 37B

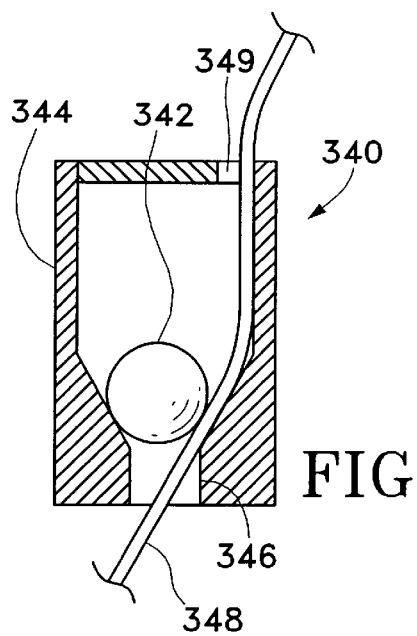
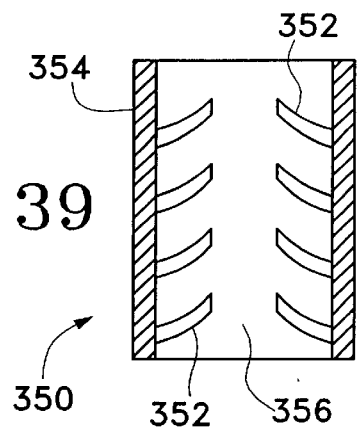
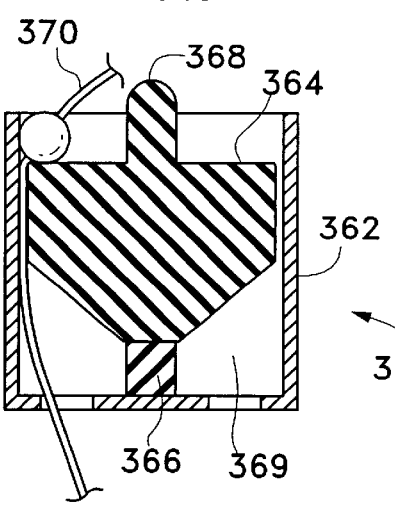
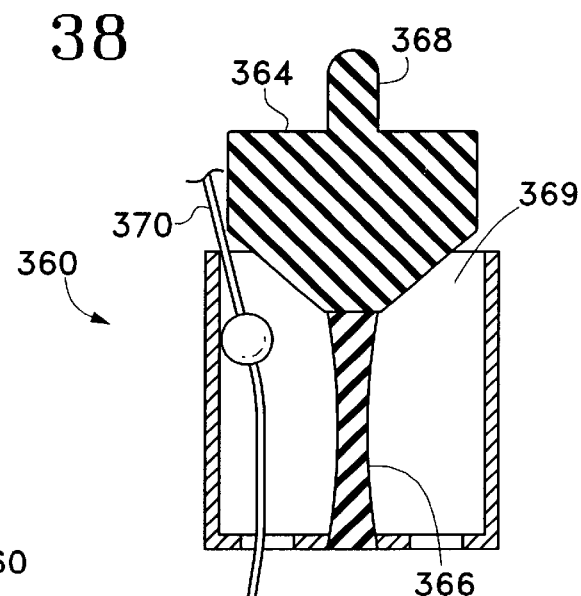
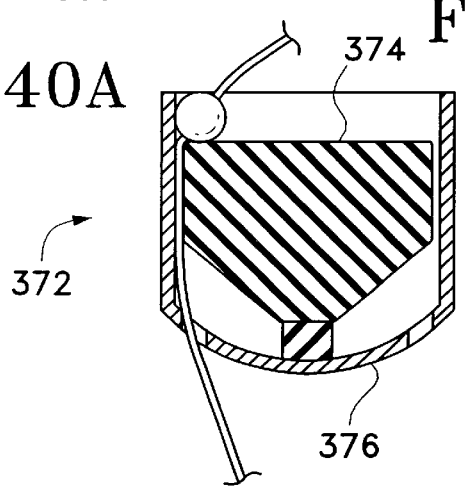
FIG. 38
FIG. 39
FIG. 40A
FIG. 40B
FIG. 41

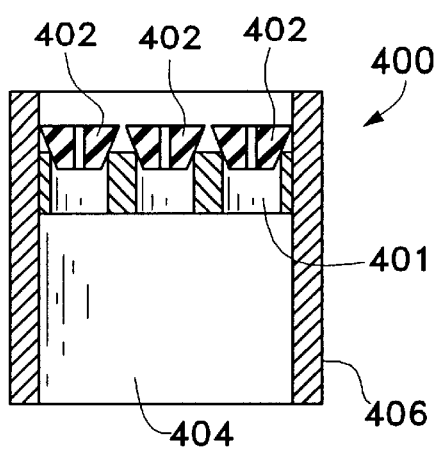
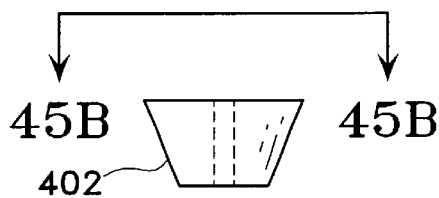
FIG. 45A
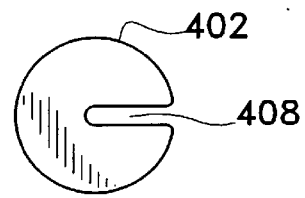
FIG. 45B
FIG. 44
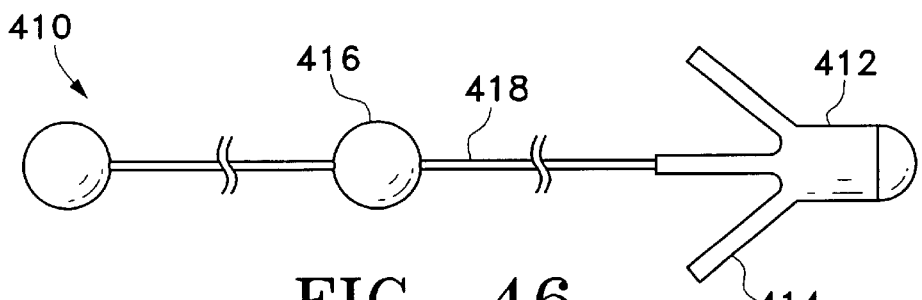
FIG. 46
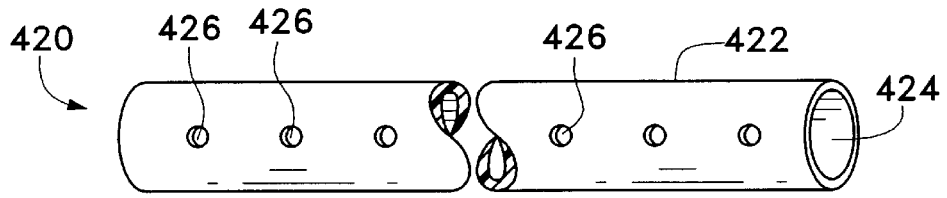
FIG. 47
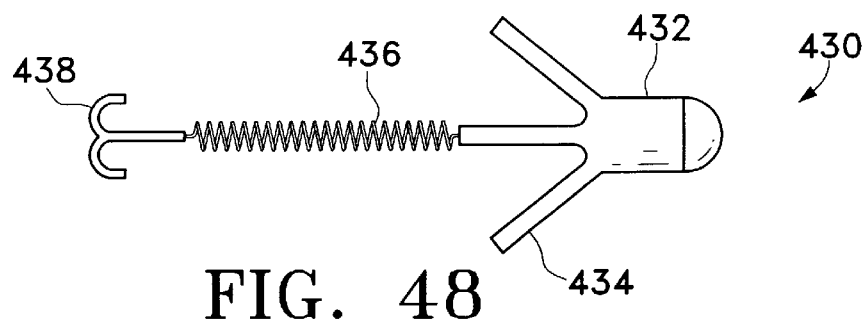
FIG. 48

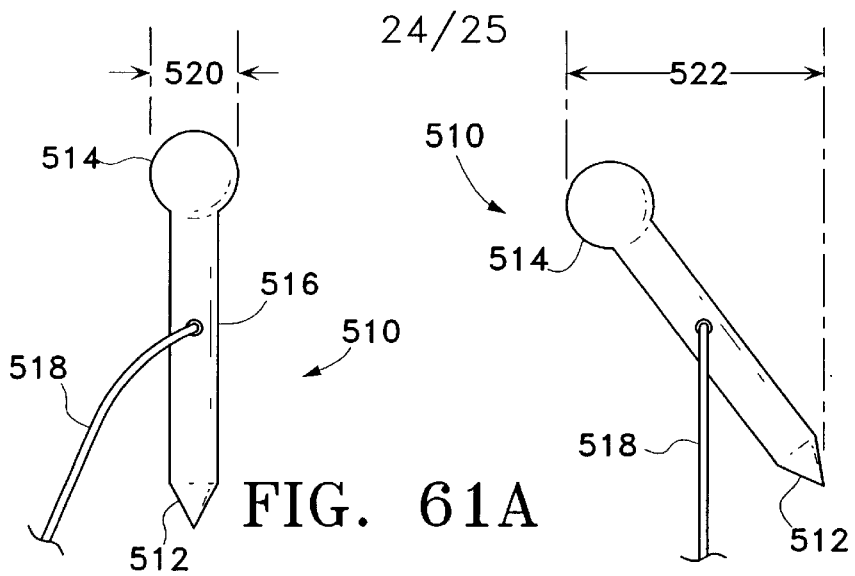
FIG. 61A
FIG. 61B
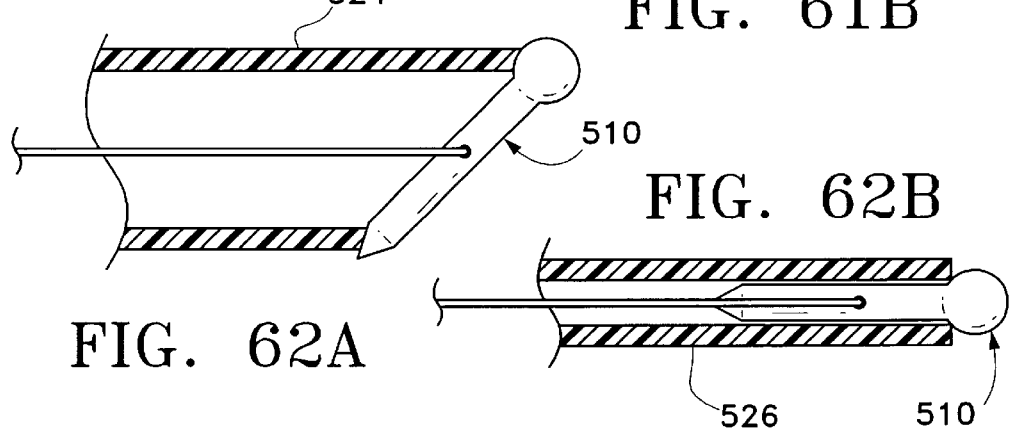
FIG. 62A
FIG. 62B
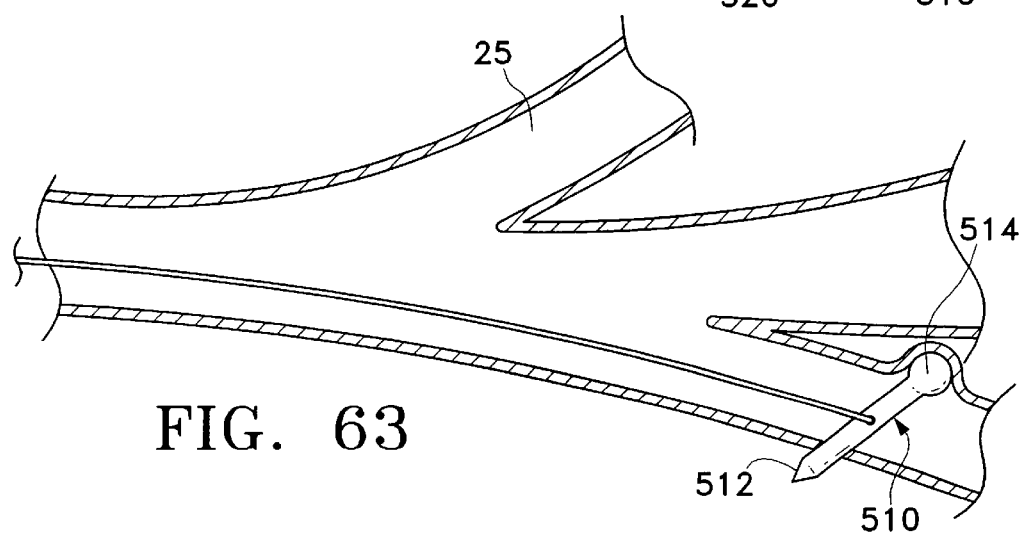
FIG. 63

US 6,599,311 B1

METHOD AND ASSEMBLY FOR LUNG VOLUME REDUCTION

This is a Continuation-in-part application of U.S. application Ser. No. 09/092,727 filed Jun. 5, 1998, now U.S. Pat. No. 6,174,323, which is incorporated herein by reference in its entirety.

BACKGROUND OF THE INVENTION

1. Field of the Invention

The present invention relates to a method and assembly for reducing the volume of a lung and, more particularly, to a mechanical lung volume reduction system comprising cords and anchors that pull on portions of a lung to compress the volume of a portion of the lung.

2. Background Information

The lungs deliver oxygen to the body and remove carbon dioxide. Healthy lung tissue includes a multitude of air passageways which lead to respiratory bronchioles within the lungs. These airways eventually lead to small sacs called alveoli, where the oxygen and carbon dioxide are exchanged through the ultra-thin walls of the alveoli. This occurs deep within the lungs, in an area which is accessed by a network of airways, consisting of a series of branching tubes which become narrower, shorter, and more numerous as they penetrate deeper into the lungs. As shown in FIG. 1, tiny air sacs called alveoli 1 surround both alveolar ducts 2 and respiratory bronchiole 3 throughout the lung. The alveoli are small, polyhedral recesses composed of a fibrillated connective tissue and surrounded by a few involuntary muscular and elastic fibers. These alveoli 1 inflate and deflate with air when we breathe. The alveoli are generally grouped together in a tightly packed configuration called an alveolar sac. The thin walls of the alveoli 1 perform gas exchange as we inhale and exhale.

During inhalation, as the diaphragm contracts and the ribs are raised, a vacuum is created in the chest, and air is drawn into the lungs. As the diaphragm relaxes, normal lungs act like a stretched balloon and rebound to the normal relaxed state, forcing air out of the lungs. The elasticity of the lungs is maintained by the supportive structure of the alveoli. This network of alveoli provides strength to the airway walls, as well as elasticity to the lungs, both of which contribute to the lung's ability to function effectively.

Patients with pulmonary disease have reduced lung capacity and efficiency due to the breakdown of lung tissue. This often is caused by smoking. In cases of severe chronic pulmonary disease, such as emphysema, lung tissue is destroyed, reducing the strength of the airways. This reduction and strength of the airway walls allows the walls to become "floppy" thereby losing their ability to remain open during exhalation. In the lungs of an emphysema patient, illustrated in FIG. 2, the walls between adjacent alveoli within the alveolar sac deteriorate. This wall deterioration is accelerated by the chemicals in smoke which affect the production of mucus in the lungs. Although the break down of the walls of the alveoli in the lungs occurs over time even in a healthy patient, this deterioration is greatly accelerated in a smoker causing the smoker's lungs to have multiple large spaces 4 with few connecting walls in the place of the much smaller and more dense alveoli spaces 1 in healthy lung tissue.

A cross section of a diseased emphysematous lung will look like Swiss cheese due to the deterioration of the alveoli walls which leaves large spaces in the tissue. In contrast, a cross section of healthy lung tissue has few or no noticeable holes because of the small size of the alveoli. When many of the walls of the alveoli 1 deteriorate, as shown in FIG. 2, the lung has larger open spaces 4 and a larger overall volume, but has less wall tissue to achieve gas exchange.

In this diseased state, patients suffer from the inability to get the air out of their lungs due to the collapse of the airways during exhalation. As a result, heavily diseased areas of the lung become over-inflated with the air that cannot escape due to the collapse of the airways. This air remains in the lung and is non-functional as it does not aid in the blood-gas exchange process. Because the lungs are limited to the confines of the chest cavity, this over-inflation restricts the in-flow of fresh air and hampers the proper function of healthier tissue. As a result of the over-inflation, patients experience significant breathlessness. Thus, the emphysema patient must take in a greater volume of air to achieve the same amount of gas exchange as a healthy individual. However, individuals suffering from emphysema still have insufficient gas exchange even when they take in as much air as their chest cavity can accommodate. Emphysema patients will often look barrel-chested and their shoulders will elevate as they strain to make room for their over-inflated lungs to work.

In cases of severe emphysema, lung volume reduction surgery (LVRS) improves lung efficiency of the patient and allows the patient to regain mobility. In lung volume reduction surgery, a diseased portion of an emphysematous lung having a large amount of alveolar wall deterioration is surgically removed as illustrated in FIG. 3. LVRS is performed by opening the chest cavity, retracting the ribs, stapling off, and removing the more diseased portion of the lung 31. This allows the remaining healthier lung tissue to inflate more fully and take greater advantage of the body's ability to inhale and exhale. Since there is more inspired air there is increased gas exchange in the healthier portion of the lung. As a result lung efficiency improves.

Lung volume reduction surgery is an extremely invasive procedure requiring the surgical opening of the chest cavity and removal of lung tissue. This surgery has substantial risks of serious post-operative complications, such as pneumothorax, and also requires an extended convalescence.

Accordingly, it is desirable to achieve the benefits of improved air exchange for emphysema patients provided by LVRS without invasive open chest surgery and the associated complications.

SUMMARY OF THE INVENTION

The present invention relates to a lung volume reduction device comprising at least one anchor having a reduced profile and being configured to assume an expanded profile wherein in the reduced profile the anchor is capable of being advanced into an airway of the lung and in the expanded profile the anchor secures to lung tissue, the anchor having at least one connector, at least one cord having a proximal end and a distal end, the proximal end being attached to at least one of the connectors and the distal end being attached to at least one of the anchors, and a delivery device being configured to removably seat at least one of the anchors on a distal end.

The present invention includes an anchor for use with the lung volume reduction device where the anchor comprises a central portion and an attachment portion connected to the central portion, the attachment portion being moveable between a reduced profile and an expanded profile, wherein when in the reduced profile the anchor is capable of being advanced into a passageway of the lung and when in the expanded profile the attachment portion attaches to the lung; and at least one cord having a distal end and a proximal end, the distal end being attached to the central portion of the anchor and the proximal end secured to the connector.

A variation of the invention includes an anchor comprising a wire where rotation of the anchor in a lung passageway permits ends of the wire to contact lung tissue causing the anchor to assume an expanded profile.

Another variation of the invention includes an anchor comprising a segment having a first and second end, wherein the central portion of the anchor is located between the first and second ends, the first end may be configured to be atraumatic and the second end may be configured to penetrate lung tissue, wherein rotation of said anchor in the lung passageway permits the ends to contact lung tissue causing the anchor to assume the expanded profile.

Another variation of the invention includes an anchor comprising a flat spring, the ends of the spring comprising the attachment portion, the spring folded about a center point, the fold forming the central portion of the anchor.

Another variation of the invention includes an anchor with an attachment portion comprising at least one tine, each the tine having a first end and a second end, the first end being attached to the central portion, wherein when the second ends of the tine moves away from the central portion the anchor assumes the expanded profile. The invention may include varying the number of tines as needed, for example, two, three, or four tines may be used.

The invention further includes providing a fibrosing agent on an anchor. The fibrosing agent may be, for example, on a surface of the anchor or adjacent to the attachment portion of the anchor.

Another variation of the anchor includes sizing the anchor so that it may enter an airway of less than 3 mm in approximate diameter. The inventive anchor may include tines is configured to prevent movement of the anchor relative to the airway when the anchor is in the expanded profile. The anchor may be configured to be atraumatic to the lung.

Another variation of the invention includes an anchor that is mechanically deformable to assume the expanded profile. In another variation, an anchor may be comprised of a shape memory alloy and the anchor is thermally deformable to assume the expanded profile. A variation of the anchor may also include one that is spring biased to assume the expanded profile.

Another variation of the invention includes an anchor with a the cord further comprising a wedge attached to a distal end of the cord, and where there are at least two tines, and the wedge being slidably attached to the anchor between at least two of the tines, when the wedge is proximate to the second end of the tines the anchor is in the reduced profile, and when the wedge slides towards the central portion of the anchor, the wedge displaces the tines so that the anchor assumes the expanded profile. This variation may also include stops that fixedly attach the wedge adjacent to the central portion.

Another variation of the invention includes an anchor that further comprises at least one covering having a wall, the wall having a plurality of openings, the covering being placed over the central portion, the second end of the tine extending through the openings of the covering, wherein movement of the central portion within the covering advances or retracts the second end of the tine through the openings.

Another variation of the invention includes a cord as previously described further including a hook attached to a proximal end of the cord.

Another variation of the cord includes a cord comprised from an elastic material, and/or a cord comprising a tube having a lumen. Another variation of the cord includes a cord having at least two segments having different diameters.

The present invention also includes a delivery device for use with the lung volume reduction device where the delivery device comprises an elongate member having a distal and a proximal end, the elongate member being sized to advance within the airway of the lung, the elongated member being configured to removably seat the anchor on a distal end of the elongated member.

A variation of the invention includes a delivery device with an elongated member further comprising a fluid delivery port at a proximal end of the elongated member, a lumen extending between the proximal and distal ends of the elongated member, and a seal in the lumen at the proximal end, the seal configured to allow the cord to exit from the proximal end while keeping the lumen fluidly sealed at the proximal end.

Another variation of the invention includes a delivery device where the distal end of the elongated member comprises a tapered section, the distal end being configured so that retracting the anchor in a proximal direction over the tapered section causes the anchor to expand to assume the expanded profile.

A variation of the delivery device may also include a distal end comprising a compressible sleeve located between the anchor and the elongate member, compressing the sleeve in a lengthwise direction causes the sleeve to expand to an increased diameter, expansion of the sleeve to the increased diameter mechanically deforms the anchor to assume the expanded profile.

Another variation of the invention may include a delivery device comprising a cutter being configured to severe a cord. The cutter may include a suture cutter, a blade within the elongated member, a flexible rod having a sharpened end, a heating element, and/or a first and second shearing surfaces.

In one variation of a cutter having a first and second shearing surfaces, the elongate member may comprise the first shearing surface and the second shearing surface may be moveable within the elongated member such that the section of the cord between the first and second shearing surfaces is cut as the shearing surfaces join. A variation of the invention includes a cutter configured such that the second shearing surface moves at least axially or at least torsionally within the elongate member.

The present invention also includes a connector for use with the lung volume reduction device comprising a body having at least one passageway sized to permit passage of the cord, and a stop having at least a portion connected to each of the passageways the stop configured to prevent movement of the cord after the cord is fed through the passageway to a desired location.

A variation of the invention may include a connector as described above wherein the body is plastically deformable such that deformation of the body reduces a diameter of the passageway to create the stop.

Another variation may include a connector wherein the stop comprises at least one tapered plug having a first and second diameters and at least one ring having an inner diameter sized between the first and second diameters of the plug, the ring located co-axially with each of the passageways, wherein movement of the at least one cord may be prevented by passing the at least one cord through the ring and inserting the tapered plug into the ring.

Another variation of the connector may include a tube removably located within the passageway of the connector where the tube permits passage of the cord. In one variation, the connector may have a plurality of stops and removal of the tube allows the stops to frictionally hold the cord within the connector. In another variation, the connector may have a moveable section having a hole sized to permit passage of the cord, the moveable section having an aligned position such that the hole is in alignment with the passageway which allows movement of the cord, and a non-aligned position such that the hole is not in alignment with the passageway which prevents movement of the cord. In this variation, the moveable section may be biased to assume the non-aligned position. In this variation, the tube may be used to retain the moveable section in the aligned position.

Another variation of the invention includes a connector having body comprised of a spring having a plurality of turns, the plurality of turns comprising the stops where the at least one cord is woven through at least one of the turns, wherein the spring has an relaxed state where the turns compress against the cord to prevent movement of the cord.

In another variation of the invention, the stop of the connector comprises a section of reduced diameter in the passageway. The connector may further include a flange within the passageway, the flange having a plurality of slots radially extending from a central opening, wherein the center opening comprises the section of reduced diameter and is sized to permit movement of the cord and the slots are sized to prevent movement of the cord. Another variation of the invention may include a connector having a stop which further comprises a plug which seats in the section of reduced diameter to provide frictional resistance against the cord to prevent movement of the cord. The plug may be directionally biased towards the section of reduced diameter by a spring.

Another variation of the invention may include a connector as described above wherein the passageway further comprises a plurality of prongs extending away from the body towards a center of the passageway, the prongs configured to retain the proximal end of the cord or to interfere with the cord and hold it in place by frictional forces.

Another variation of the invention may include a connector as described above wherein the stop of the connector comprises a stopper slidably located within the passageway and attached to the body by a spring element such that the stopper is maintained in the passageway and is temporarily moveable out of a proximal end of the body, the stopper having a proximal diameter less than a diameter of the passageway, wherein after a segment of increased diameter of a cord is pulled from a distal end of the body through the proximal end of the body and past the stopper, the stopper prevents substantial movement of the cord in a distal direction.

The invention further includes a method for minimally invasively or non-invasively treating a lung having at least an emphysematous portion comprising the step of improving a pulmonary function of at least a first portion of the lung. Improving a pulmonary function of at least a first portion of the lung may include reducing hyperinflation of a second portion of the lung, increasing the range of motion of the diaphragm, redirecting airflow to a healthier portion of the lung, and/or reducing a volume of a second portion of the lung to remove non-functional residual air from the lung.

Another variation of the invention includes a method a method for minimally invasively or non-invasively treating a lung having at least an emphysematous portion comprising the step of improving a pulmonary function of at least a first portion of the lung wherein the step of improving a pulmonary function of at least the first portion of the lung comprises the steps of attaching a first anchor to the lung, attaching a second anchor to lung, connecting a cord between the second anchor and the first anchor; and shortening the length of the cord between the first and second anchors to compress a second portion of the lung. The method may include the step of deflating at least a portion of the lung prior to the shortening step. The method may include the step of injecting a sclerosant agent in the second portion of the lung to maintain compression of the second portion. And, the connecting step described above may include using a connector to join separate cords of the first and second anchor.

The invention also includes the method described above with the additional step of placing at least one support member in the lung to create an area of improved anchor support for increasing the ability of the anchors.

The invention also includes a lung volume reduction device kit comprising the lung volume device as described above and a bronchoscope, and/or a fibrosing agent.

The invention also includes a method for preparing the lung volume reduction device described above for use in a medical procedure comprising the steps of sterilizing the lung volume reduction device, and packaging the lung volume reduction device.

The invention also includes a method of teaching the use of any of the devices or methods described herein.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 19 is an illustration of a portion of a lung before its volume has been compressed;

FIG. 20 is an illustration of the portion of the lung of FIG. 19 after its volume has been compressed;

FIGS. 21A–29 illustrate variations of the anchor of the present invention;

FIGS. 30–33B illustrate variations of the delivery device of the present invention;

FIGS. 34–44 illustrate variations of the connector of the present invention;

FIGS. 45A–45B illustrate a plug for use a connector of the present invention;

FIGS. 46–48 illustrate variations of the cord for use with anchors of the present invention;

FIGS. 61A–61B illustrate a further variation of an anchor of the present invention;

FIGS. 62A–62B illustrate a further variation of a delivery device of the present invention;

FIG. 63 illustrates deployment of the anchor variation depicted in FIGS. 61A and 61B.

DETAILED DESCRIPTION OF THE PREFERRED EMBODIMENTS

The present invention pertains to a method and assembly to relieve the effects of emphysema and other lung diseases by increasing the efficiency of gas exchange in the lung. This is achieved by compressing the volume of a portion of the lung, preferably a diseased portion of the lung tissue. Compressing the volume of a portion of the lung redistributes the remaining lung tissue to allowing the tissue to inflate more fully. The reduction in volume of the portion of the lung also increases the range of motion of the diaphragm and chest wall thereby improving lung efficiency.

Figure 1:
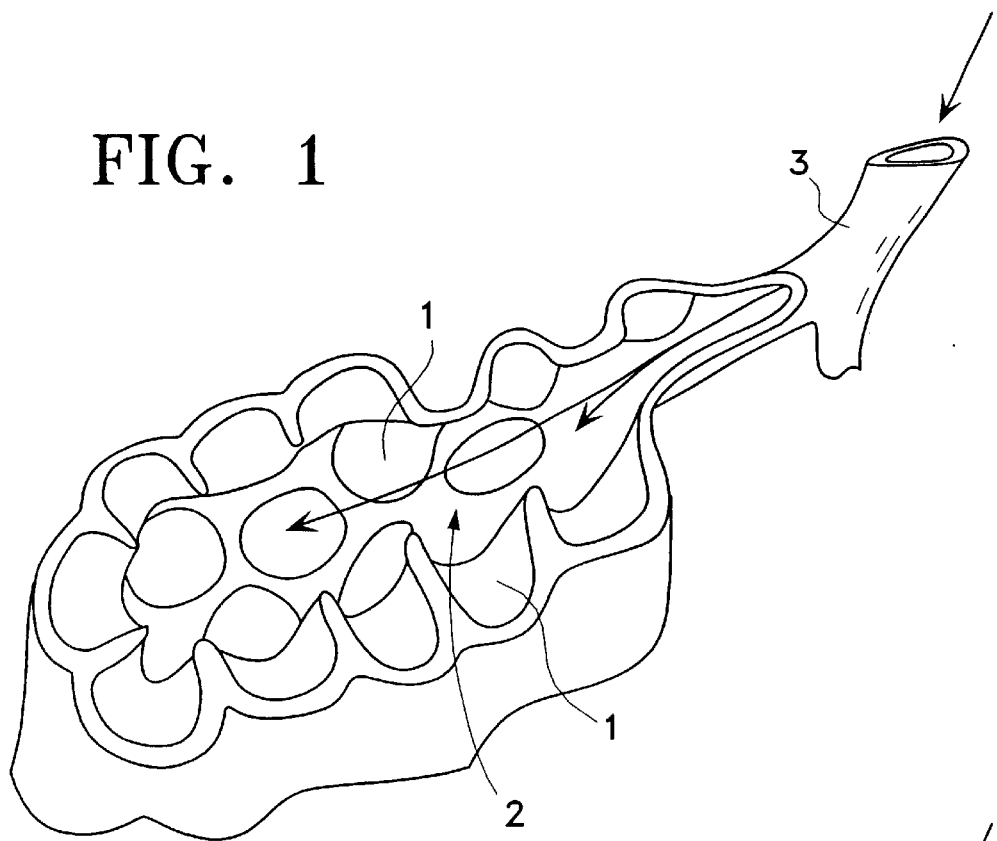
FIG. 1 is a cross sectional view of an alveolar sac of a healthy lung.
Figure 2:
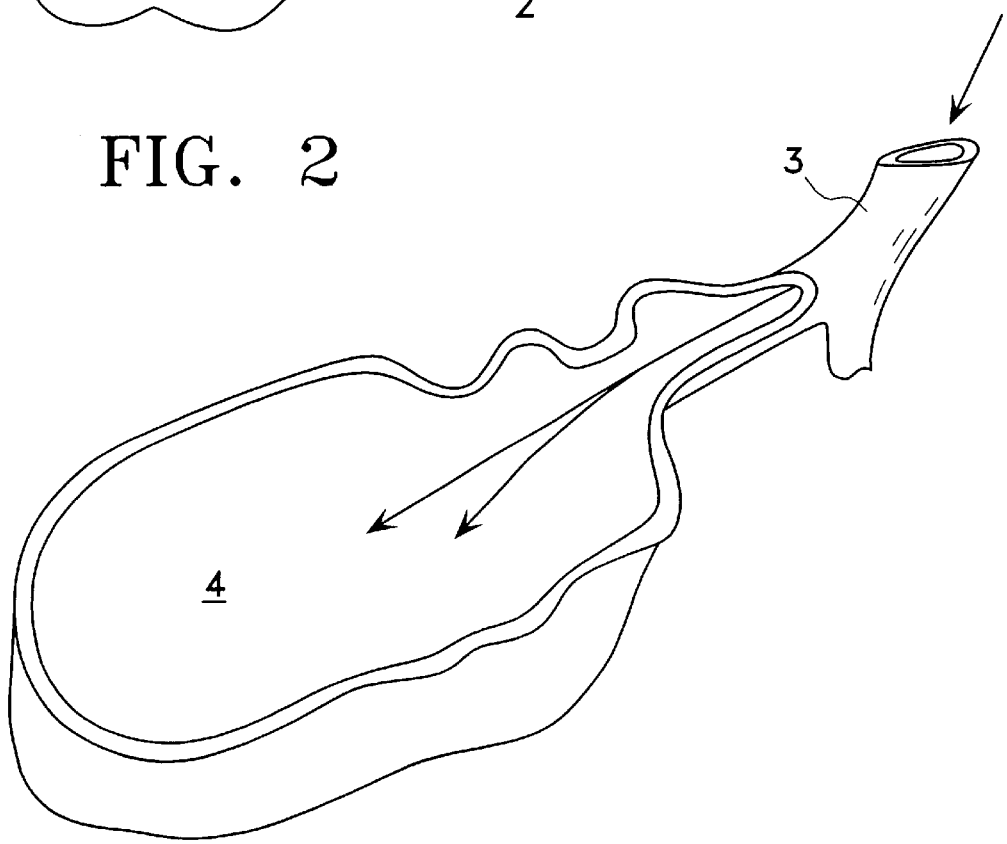
FIG. 2 is a cross sectional view of an alveolar sac of a diseased lung.
Figure 3:
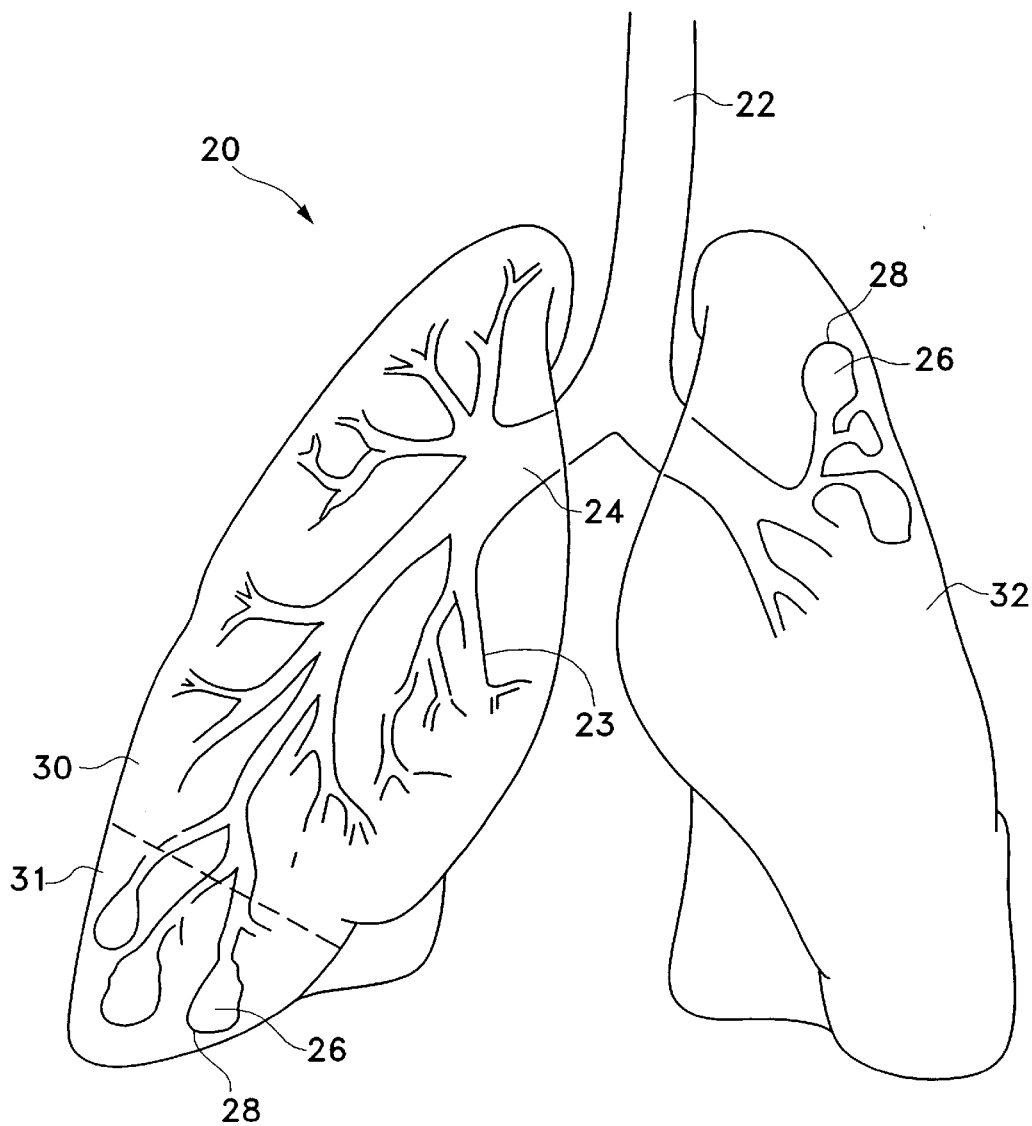
FIG. 3 is an illustration of a lung having a diseased lower portion prior to surgery.

FIG. 3 illustrates human lungs 20 having a left lung 32 and a right lung 30. A diseased portion 31 is located at the lower portion or base of the right lung 30 (indicated by the volume of the lung below the dashed line on the right lung). However, the diseased portions of an unhealthy lung may not be located in discrete areas. As illustrated in FIG. 3, the trachea 22 extends down from the larynx and conveys air to and from the lungs. The trachea 22 divides into right and left main bronchi 24, which in turn form lobar, segmental, and sub-segmental bronchi or bronchial passageways. Eventually, the bronchial tree 23 extends to the terminal bronchiole. At the terminal bronchiole, alveolar sacs 26 containing alveoli 28 perform gas exchange as humans inhale and exhale.

As illustrated in FIG. 3, the diseased portion 31 of the lung 30 is located at the lower portion or base of the lung. By way of example, it can be considered that this diseased portion 31 has been stricken by emphysema. The emphysematous portion 31 of the lung 30 generally includes sections in which the walls between the adjacent alveoli 28 have deteriorated to a degree that the lung tissue looks like Swiss cheese in cross section. When this occurs, pulmonary function is significantly impaired due to reduced total surface area of alveolar wall tissue which serves as the gas exchange mechanism of the lung. Because of emphysema, the diseased portion of the lung also contributes to the loss of it's the lung's elastic recoil properties. Thus, the lung also experiences a loss in the force used to expel air during expiration. The present invention strives to relieve the effects of emphysema by increasing the lung's 30 efficiency to perform gas exchange. As described below, the present invention increases the range of motion of the diaphragm and chest wall by compressing the volume of a portion of the lung occupied in the thoracic cavity to redistribute the remaining healthier lung tissue, thus improving the efficiency of gas exchange in the lung.

The following illustrations are examples of the invention described herein. It is contemplated that combinations of aspects of specific embodiments or combinations of the specific embodiments themselves are within the scope of this disclosure. Likewise, it is intended that the devices described herein may be used to perform the various methods also described herein.

According to one variation of the present invention, a volume of a portion of a diseased lung is compressed or reduced by locating an anchor in a bronchial passageway of the lung, and pulling on the anchor to collapse the lung tissue surrounding the anchor to compress the volume of a portion of the lung. Preferably, a plurality of anchors are used to assist in collapsing an area of the lung tissue. It is also contemplated that instead of placing anchors in the airways, the anchors may be deployed exterior to the lung. Once anchors have been placed, they are drawn together and compress lung tissue. It is believed that the lung has an ability to seal small holes formed in the lung tissue as a result of the placement of the anchors.

Figure 4:
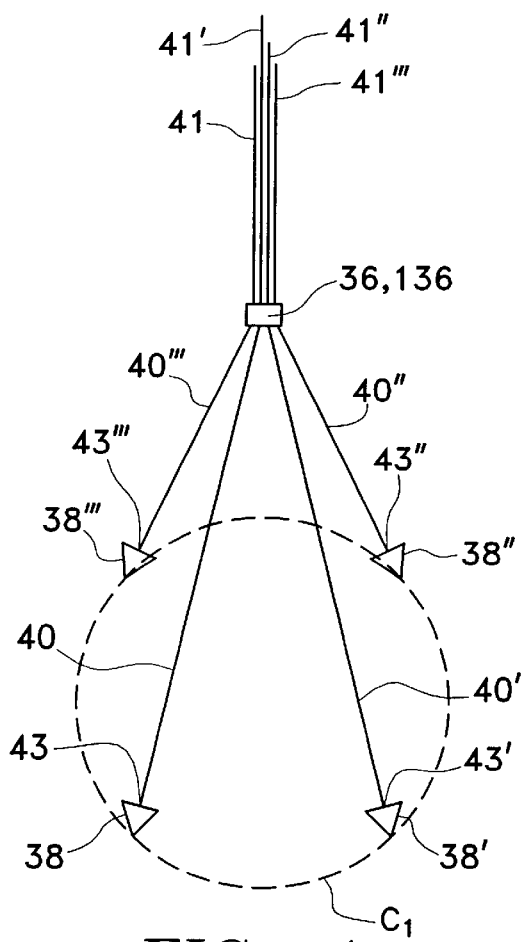
FIG. 4 is a perspective view of a plurality of anchored anchors before being pulled to compress the volume of a portion of a lung.
Figure 6:
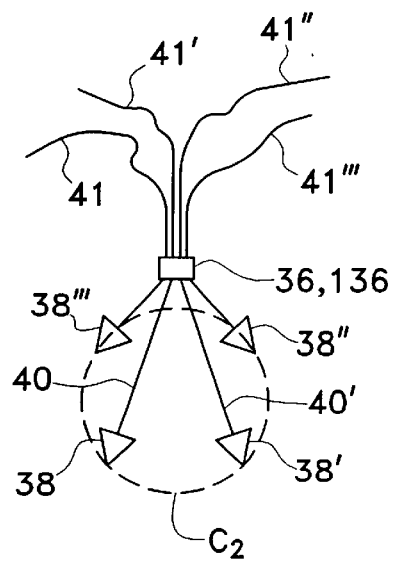
FIG. 6 is a perspective view of a plurality of anchored anchors after being pulled to decrease the compress the volume of a portion of a lung according to one embodiment of the present invention.
Figure 5:
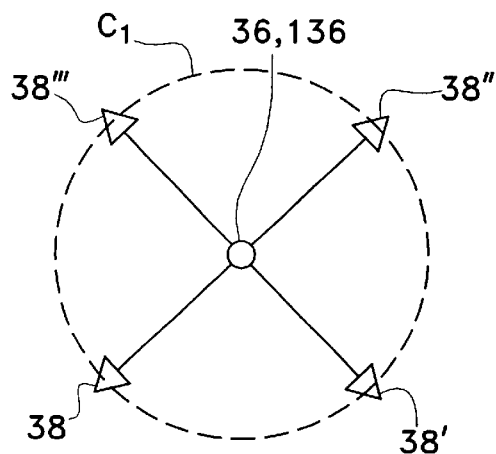
FIG. 5 is a top view of the plurality of anchored anchors shown in FIG. 4.
Figure 7:
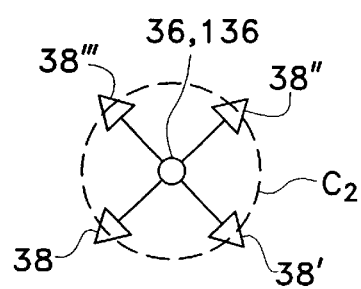
FIG. 7 is a top view of the plurality of anchored anchors shown in FIG. 6.

FIGS. 4–7 illustrate the general concept of the present invention. FIGS. 4 and 5 represent a time $t_1$, and FIGS. 6 and 7 represent a later point in time $t_2$. At time $t_1$, a plurality of anchors 38, 38', 38", 38'" are located at different positions in the lung. The anchors 38, 38', 38", 38'" are anchored, fixed, or firmly attached to the lung (not illustrated) at their respective different positions. Thus, the area of the lung that is immediately surrounding each anchor will move when the respective anchor is moved.

The anchors 38, 38', 38", 38'" are equally spaced as shown in FIGS. 4 and 5. However, the anchors may be located at various positions in the lung so as to not be evenly or equally spaced and still function to compress the volume of a portion of the lung as described herein. Attached to each of the anchors 38, 38', 38", 38'" is a cord 40, 40', 40", 40'" which can be in the form of a string, fiber, filament, rubber band, coil spring, or the like. Each of the cords 40, 40', 40", 40'" has a free end 41, 41', 41", 41'" and an attached end 43, 43', 43", 43'". The attached end 43, 43', 43" 43'" of each cord is that end of each respective cord 40, 40', 40", 40'" that is attached or tethered to the respective anchors 38, 38', 38", 38'". The free end 41, 41', 41", 41'" of each cord 40, 40', 40", 40'" is the furthest end of each respective cord not attached to the respective anchors 38, 38', 38", 38'".

As shown in FIGS. 4–7, the anchors 38, 38', 38", 38'" generally lie along the circumference of a circle $C_1$. Although the anchors 38, 38', 38", 38'" are illustrated as lying along the circumference of a circle, the anchors can be located in other configurations. Thus, the anchors can be anchored in different planes and spaced apart from each other in a variety of different configurations.

The circle $C_1$ has an area $A_1$. Each of the cords 40, 40', 40", 40'" is attached to a respective anchor 38, 38', 38", 38'". For example, the cord 40' is attached to the anchor 38'. Each of the cords 40, 40', 40", 40'" is connected to a connection device 36. The connection device 36 connects, knots, unites, bonds, fastens, glues, wedges, attaches, or fixes together the cords 40, 40', 40", 40'" such that when one of the cords 40 attached to an anchored anchor 38 is pulled in tension, the other cords 40', 40", 40'" may also be placed in tension. The connection device 36 is thus connected to the first anchor 38 by the first cord 40 and is connected to the second anchor 38' by the second cord 40'. In essence, when two cords 40, 40' are connected by the connection device 36, the two cords 40, 40' between the two anchors 38, 38' and the connection device 36 together function as or define one cord connecting to the two anchors 38, 38'. Thus, the connecting device 36 can be a clasp, clamp, cinch, snap, knot, clip, chock, self-locking device, or the like.

The first cord 40 has a first cord length measured between the first anchor 38 and the connection device 36. The second cord 40' has a second cord length measured between the second anchor 38' and the connection device 36. The other cords 40", 40'" have cord lengths measured between the respective anchor and the connection device 36. The connection device 36 prevents each of the cord lengths from increasing, i.e., prevents the anchors from returning to their original anchored positions. The embodiment of the connection device 36 illustrated in FIGS. 4–7 is a self-locking device, described further below, that permits each of the cords 40, 40', 40", 40'" to traverse away from the self-locking device in a direction toward the free ends 41, 41', 41", 41'", but prevents each of the cords from traversing away from the self-locking device in a direction toward the attached ends 43, 43', 43", 43'". The cords 40,40', 40", 40'" pass through an opening in the self locking device.

The cords 40, 40', 40", 40'" illustrated in FIGS. 4 and 5 have been pulled taut. That is, the cords 40, 40', 40", 40'" have been pulled or drawn tight and are not slack. However, at the time $t_1$ illustrated in FIG. 4., the anchors, and surrounding lung tissue, have not been moved. Thus, the lung has not been compressed and the volume has not been changed. However, after the cords 40, 40', 40", 40'" are taut and the cords are pulled or further tensioned, the distance between the anchors 38, 38, 38", 38'" will decrease. The lung tissue surrounding each anchor 38, 38', 38", 38'" moves with the respective anchor such that the lung tissue between each anchor and the connection device will physically collapse or compress. The connection performed by the connection device 36 may occur while the distance between the anchors 38, 38', 38", 38'" is decreased, or after the distance between the anchors has been decreased to a desired distance. According to one embodiment of the present invention, a self-locking device is moved toward the anchors 38, 38', 38", 38'" to cause the distance between the anchors to decrease, and at each point along the path of movement of the connection device a connection between the cords 40, 40', 40", 40'" is defined.

Thus, as illustrated by FIGS. 6 and 7, at time $t_2$, the anchors 38, 38', 38", 38'" and surrounding lung tissue have been moved toward each other (toward the center of the original circle $C_1$) to define a second circle $C_2$ having a smaller diameter than the circle $C_1$. At time $t_2$ the anchors 38, 38', 38", 38'" generally lie along the circumference of the circle $C_2$. As described above, this may be achieved by pulling the anchors 38, 38', 38", 38'" toward each other via the cords 40, 40', 40", 40'". As described further below, the anchors can be pulled or moved toward each other by: (1) pulling the free ends 41, 41', 41", 41'" of the cords away from a connection device; (2) moving the connection device 36 toward the anchors 38, 38', 38", 38'" to pull the anchors; or (3) simultaneously moving the self-locking device toward the anchors and pulling the free ends of the cords away from the self locking device.

As illustrated in FIGS. 4–7, the connection device may not lie in the plane formed by the circles $C_1$ or $C_2$. This may be the case when it is desired to compress tissue in the direction perpendicular to the plane formed by either of the circles, or to simply compress a greater volume of tissue. In this case, it may be necessary to anchor the connection device in the lung tissue so that force can be generated in the direction perpendicular to the plane formed by either circle.

The anchoring of the connection device can be accomplished in numerous ways. A variation of the invention is illustrated in FIG. 7A. As shown, the connection device 136 is held in position by positioning the connection device at an airway bifurcation 27. In this variation, the forces exerted on the connection device 136 by the tension of the lines 40, 40', 40", 40'", may be balanced about the bifurcation 27 to keep the connection device 136 in place. In another variation of the invention, as illustrated in FIG. 7B, "wings" or "flaps" may be added to the connection device to prevent movement of the device from the bifurcation 27 of the airway. FIGS. 7C and 7D illustrate additional variations of the invention. As illustrated, the anchoring features of anchors (such as hooks, barbs, or legs) and others described herein may be added to the connection device so that the connection device can be anchored into a non-bifurcated section of airway. In such a variation, the anchoring feature may be deployed into place in a similar manner as described elsewhere for deploying an anchor.

Because the diameter of the second circle $C_2$ is smaller than the diameter of the circle $C_1$, the area of the second circle is smaller than the area of the first circle. Because the area of the second circle $C_2$ is smaller than that of the first circle $C_1$ (and the distance between the anchors 38, 38', 38", 38'" has decreased), the lung tissue near the anchors will collapse or compress inwardly toward the center of the circles $C_1$, $C_2$. Depending upon the location of the anchors 38, 38', 38", 38'", the anchors can move inwardly toward the center of the circles and slightly toward the center or interior of the lung. Because the distance between the anchors 38, 38', 38", 38'" has been decreased, the net surface area or peripheral surface of the portion of the lung is less, and the volume of the lung is less due to the collapsing or compressing of the lung tissue.

After the portion of the cords 40, 40', 40", 40'" between the connection device 36 and the anchors 38, 38', 38", 38'" is tensioned and the connection device 36 has connected the cords so as to keep the lung tissue in its collapsed condition, the remaining portion of the cords having the free ends 41, 41', 41", 41'" (the limp portions illustrated in FIG. 6) may be cut such that non-functional portions of the cords may be removed from the lungs by pulling the cords out of the mouth or nasal cavity.

Figure 8:
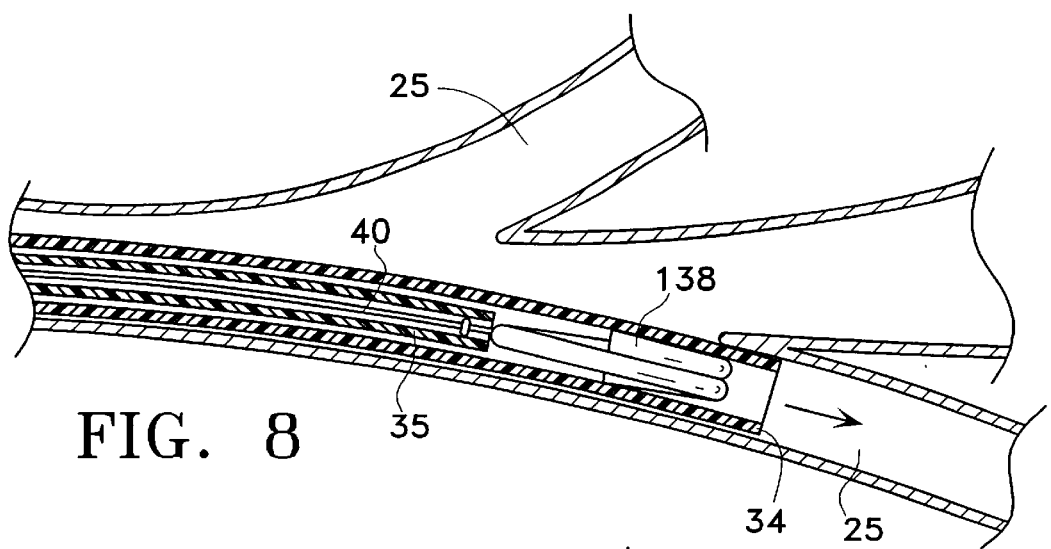
FIG. 8 is a side cross sectional view of an anchor being inserted into a bronchial passageway according to one embodiment of the present invention.
Figure 9:
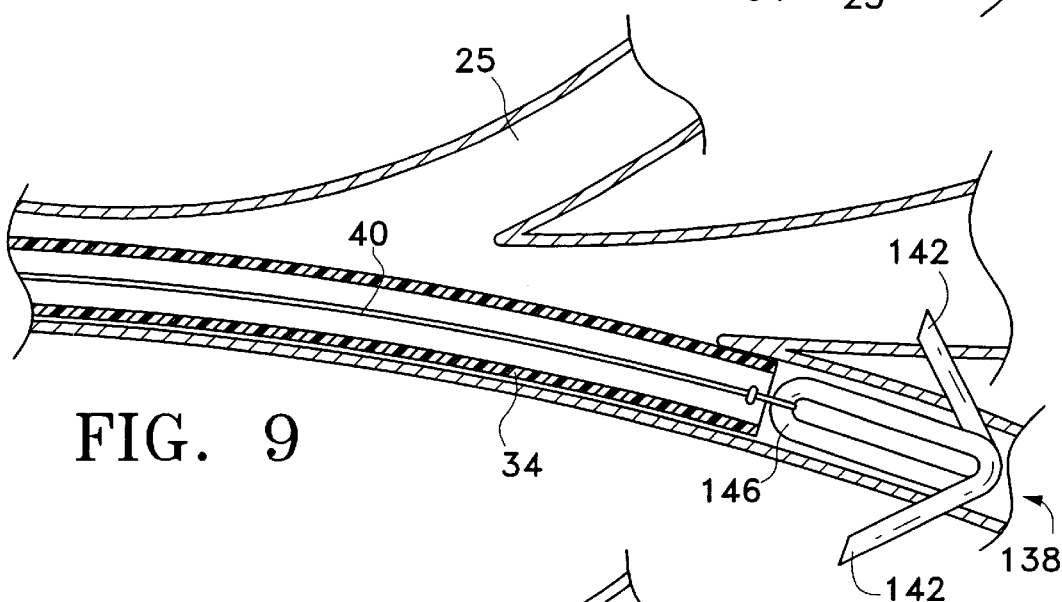
FIG. 9 is a side cross sectional view of an anchor anchored to a bronchial passageway according to one embodiment of the present invention.
Figure 10:
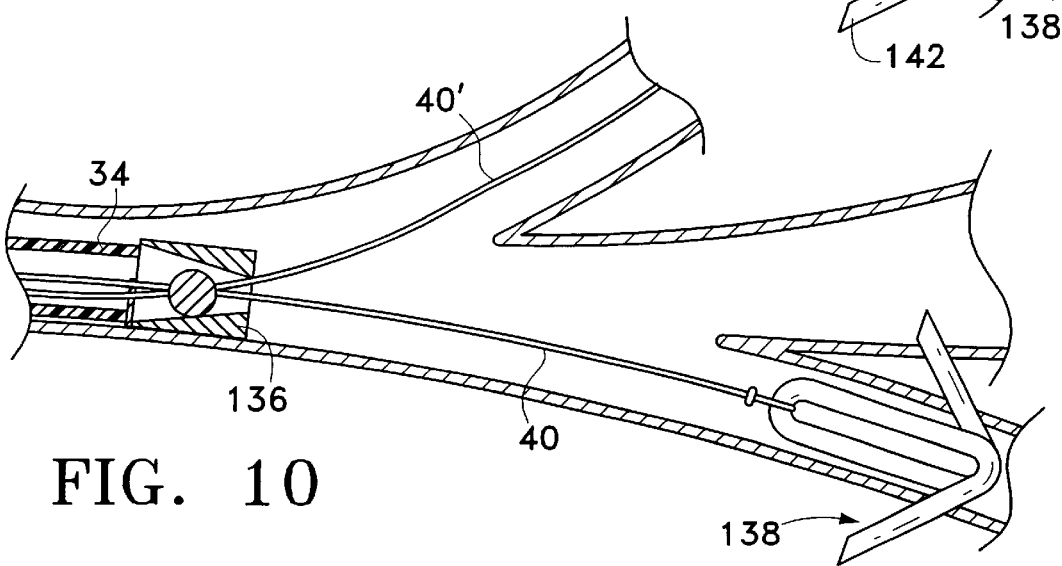
FIG. 10 is a side cross sectional view of an anchor fixed to a bronchial passageway and tethered to a self-locking device according to one embodiment of the present invention.

FIGS. 8–10 illustrate a variation of how the anchors 38, 38', are located in and fixed to the outer periphery of the bronchial tree.

As shown in FIG. 8, a delivery device 34 is sized to fit within a bronchial passageway 25. The delivery device 34 is used to deliver the anchor 38 to the outer periphery of the bronchial tree and may be a cannula, tube, bronchoscope, or another device capable of accessing the outer periphery of the bronchial tree. As described herein, the delivery device 34 may be configured to house an anchor within the delivery device 34 or the device 34 may be configured to removably seat an anchor on an outside of the device 34. Specifically, as shown in the variation of FIG. 8, the anchor 38 to be delivered to the outer periphery of the bronchial tree may be located inside the delivery device 34. It is preferred that the delivery device be fed into the lungs through a bronchoscope. It is also possible for the bronchoscope to be used as the delivery device. After the proper location has been determined with the bronchoscope, the anchor 38 is delivered as described below.

According to the variation shown in FIG. 8, an anchor may be a V-shaped spring 138. The V-shaped spring 138 is in a collapsed state or reduced profile while it remains inside the tubular channel of the delivery device 34. When the V-shaped spring 138 is pushed outside of the delivery device 34, the V-shaped spring expands to an expanded position or expanded profile, as shown in FIG. 9. Once the V-shaped spring 138 expands, it is fixed or fastened to the walls of the bronchial passageway 25 such that the lung tissue in the vicinity of the V-shaped spring moves with the V-shaped spring. A hollow second tube or a push-device 35 having a size or diameter smaller than that of the internal diameter of the delivery device 34 is inserted into the delivery device 34 to force the V-shaped spring 138 out of the delivery device 34 into the bronchial passageway 25.

Figures 14, 15:
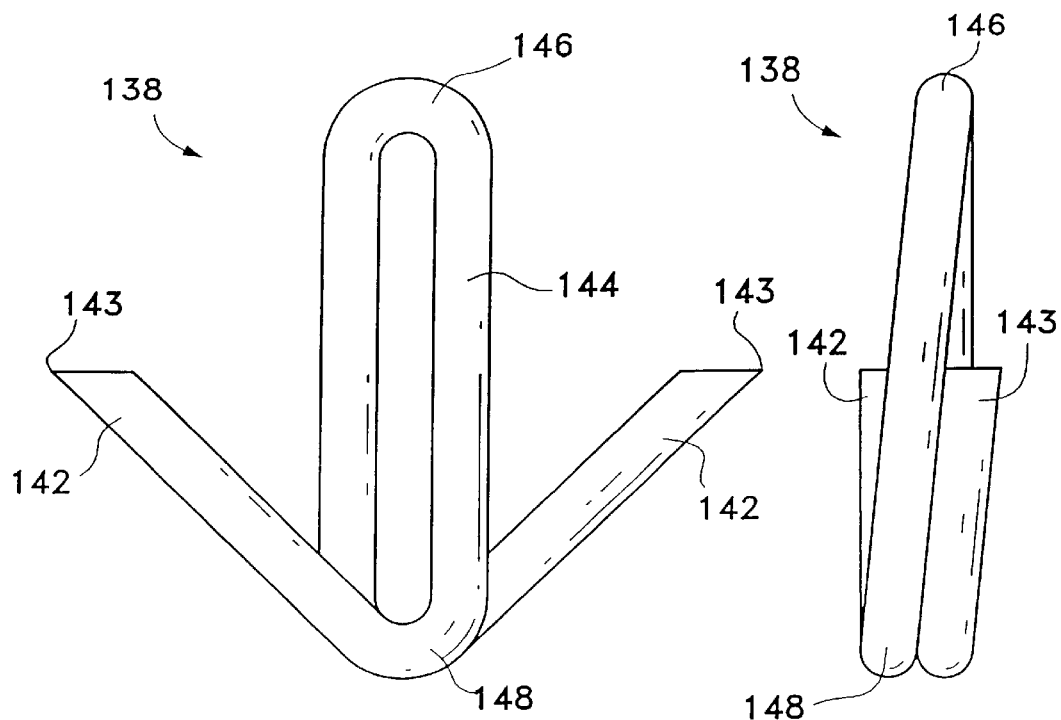
FIG. 14 is a side view of an anchor for use with the present invention.
FIG. 15 is an end view of the anchor of FIG. 14.
Figure 16:
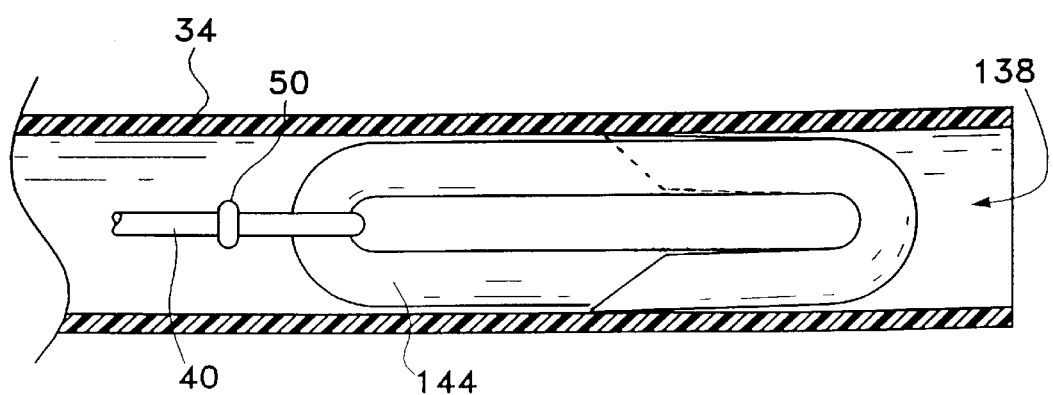
FIG. 16 is a side cross sectional view of an anchor according to one embodiment of the present invention, where the anchor is in a collapsed state and is located within a tube.

FIGS. 14–16 illustrate further details of the V-shaped spring 138. As shown in FIG. 14, the V-shaped spring 138 may be a rod shaped piece that has been bent such that it has spring-like characteristics. The V-shaped spring 138 includes an attachment portion comprising two end portions or barbs 142 that form an angle relative to a lateral or central portion 144 of the V-shaped spring when the barbs are in the extended position. The barbs 142 together define the V-shape of the V-shaped spring when the barbs are in an expanded position. Hence, the barbs 142 together define the point or vertex of the "V" at an insertion end 148 of the V-shaped spring.

The barbs 142 perform the anchoring function of the V-shaped spring 138 by wedging against the bronchial passageway to create friction or by penetrating the walls of the bronchial passageway. Because of the spring-like characteristics of the V-shaped spring, the barbs 142 strive to angle outwardly from the lateral portion 144. The V-shaped spring 138 also includes an attachment end 146 located on the lateral or central portion 144 opposite from the insertion end 148. The attachment end 146 is the location where one of the cords 40 is tethered. The barbs 142 strive to extend angularly outward from the lateral portion 144, and form an angle with respect to the lateral portion. The insertion end 148 of the V-shaped spring 138 will be the first portion of the V-shaped spring that exits the tube 34 as the push device 35 forces the V-shaped spring from the tube. The attachment end 146 of the V-shaped spring 138 is the last portion of the V-shaped spring to exit from the tube 34.

As soon as the barbs 142 extend from the tube 34, they will spring outwardly toward the walls of the bronchial passageway. The barbs 142 of the V-shaped spring 138 prevent the expanded V-shaped spring from moving in a direction opposite to the direction in which the "V" or vertex points. That is, the barbs 142 may function similarly to barbs on a fish hook, harpoon, or arrow. The barbs 142 may each include a sharp point 143 that curves or projects in a direction opposite from the direction the vertex at the insertion end 148 points. The barbs may be of any design that facilitates securing an anchor to lung tissue.

As described herein, other anchoring devices may be used to perform the anchoring function. For example, a J-hook, a mooring device, a ballooning device, and expanding polymeric plug, a stent-like device, and other various devices can be satisfactorily fastened, fixed or anchored to the bronchial passageway of a lung. Other anchors are described below. Furthermore, although the V-shaped springs include two barbs 142, the V-shaped spring can have more than two barbs or only one barb. In addition, the connection device 36 itself can also anchor to the lung. For example, two cords 40, 40' having anchors 38, 38' attached thereto can be tied to a third anchor such that the third anchor is a connection device.

FIG. 16 illustrates a side view of the V-shaped spring 138 in its collapsed position when the V-shaped spring is located within the tube 34. As shown in FIG. 16, the barbs 142 collapse toward the lateral portion 144 when the V-shaped spring 138 is positioned within the tube 34. Prior to inserting the V-shaped spring 138 into the tube 34, the cord 40 is secured to the attachment end 146 of the V-shaped spring. The cord 40 can be tethered, braided, buttoned, interlocked, wired, pinned, clasped, or joined to the attachment end 146 by any suitable means. The cord 40 may be wrapped around the attachment end 146 and secured to itself to define a loop around the attachment end 146. A clasp 50 or other similar device may be used to secure the loop around the attachment end 146.

Referring back to FIG. 8, the cord 40 has already been attached to the V-shaped spring 138 before the V-shaped spring has been located in the channel of the tube 34. Once the push device 35 pushes the V-shaped spring 138 out of the tube 34, the push device 35 is withdrawn, leaving the V-shaped spring 138 anchored or secured to the bronchial passageway 25. FIG. 9 illustrates that the cord 40 remains attached to the V-shaped spring 138 after the push device 35 has been withdrawn from the tube 34 and after the V-shaped spring has expanded. The protruding ends 42 of the V-shaped spring 138 extend into the walls of the bronchial passageway 25 such that the V-shaped spring 138 is fixedly secured to the bronchial passageway. Thus, substantial relative movement between the anchored V-shaped spring 138 and the portion of the bronchial passageway immediately adjacent the V-shaped spring does not occur; when the anchored V-shaped spring 138 moves, the surrounding tissue immediately adjacent to the V-shaped spring will move.

Once the V-shaped spring 138 is anchored in place, the tube 34 can be withdrawn from the bronchial passageway 25. Thereafter, the same procedure can be followed to deposit more V-shaped springs 138 (each having a cord 40 attached thereto) in other bronchial passageways at locations distant from the area where the first V-shaped spring was positioned. In reference to FIGS. 10–13, after the anchors 38, 38', such as V-shaped springs, have been fixed to different positions in the bronchial tree, the cords 40, 40' can be tensioned.

Figure 11:
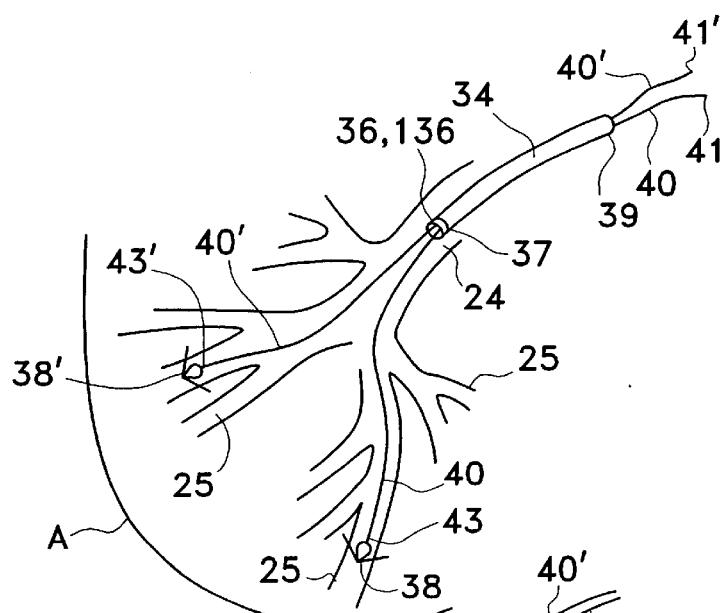
FIG. 11 is an illustration of a portion of a lung having two variations of the anchor of the present invention fixed within lung and two cords connecting the anchors.
Figure 12:
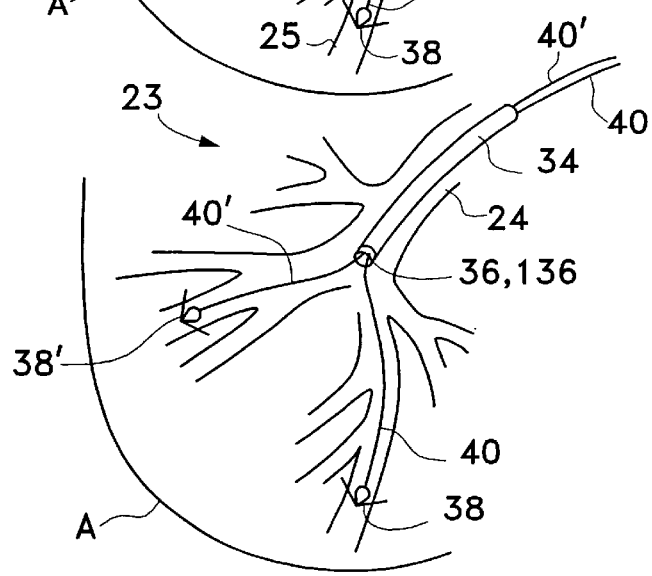
FIG. 12 is an illustration of a portion of a, lung with anchors fixed within the lung as a delivery device is advanced into the airways to reduce the length of cord between anchors.
Figure 13:
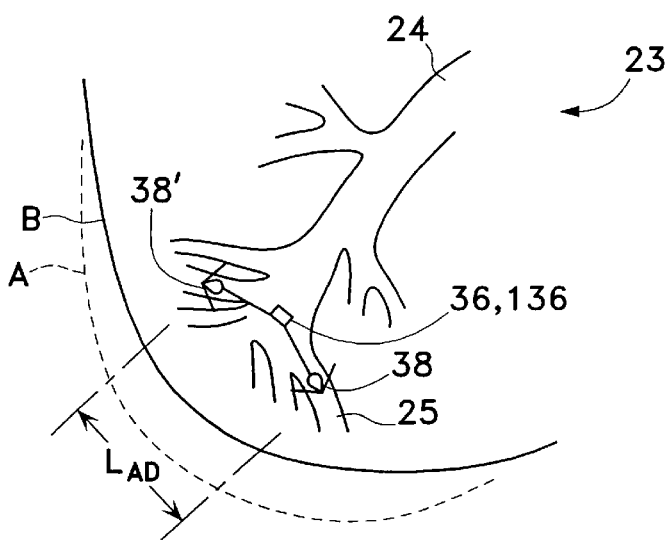
FIG. 13 is an illustration of a portion of a lung after its the volume has been reduced according to one embodiment of the present invention.

FIGS. 11–13 illustrate in further detail how the diseased portion of a lung 31 may be collapsed to reduce the volume of the lung 30.

As illustrated by FIG. 11, the bronchial tree-like pattern 23 in the lung 30 includes a multitude of bronchial passageways 25. Any of these bronchial passageways 25 may be used to insert an anchor 38 into the lung. Because the bronchial passageways 25 are hollow, it is possible to insert a delivery device 34 such as a tube, a bronchoscope, or a cannula into one bronchial passageway. As shown in FIG. 11, the lung 31 includes therein a pair of anchors 38, 38' which have been anchored or attached to two separate bronchial passageways 25 in the outer periphery of the bronchial tree 23. Attached to each of the anchors 38, 38' is a cord 40, 40' that extends from each of the anchors 38, 38' through the bronchial tree 23 and into the delivery device 34. One cord 40, 40' is tethered to each of the anchors 38, 38'. The line or cord 40, like the delivery device 34, extends through the bronchus 24 up the trachea 22 and out the mouth or nasal cavity of the patient.

As illustrated in FIGS. 11–12, the connection devices may be placed in front of, outside of, or inside the distal tip of the delivery device 34 Once the anchors 38, 38' have been positioned in the lung, the connection device 36 is positioned to cause the cords 40, 40' to be tensioned and to move the anchors 38, 38'. The connection device 36 can be used to connect the cords 40, 40' and to cause the anchor 38 to move toward the anchor 38', thereby causing the tissue adjacent the anchor 38 to move towards the lung tissue adjacent the anchor 38'.

FIG. 13 illustrates the compressed lung. After the distance between the anchors is set as desired, the cords may be cut proximal to the connection device 36, and the excess cords and delivery device may be removed from the patient. The connection device 136, the anchors 38, 38', and the shortened sections of cords 40, 40' left in place maintain the compression of the lung tissue.

Figure 17:
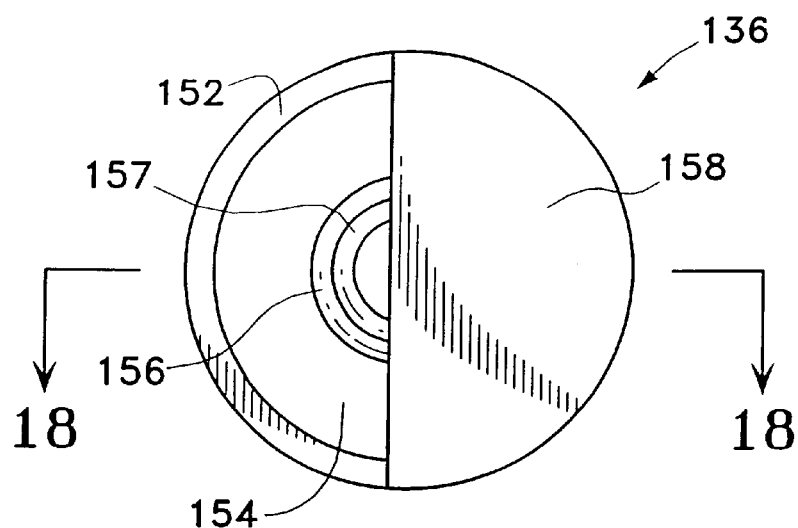
FIG. 17 is a top view of a self-locking device according to one embodiment of the present invention.
Figure 18:
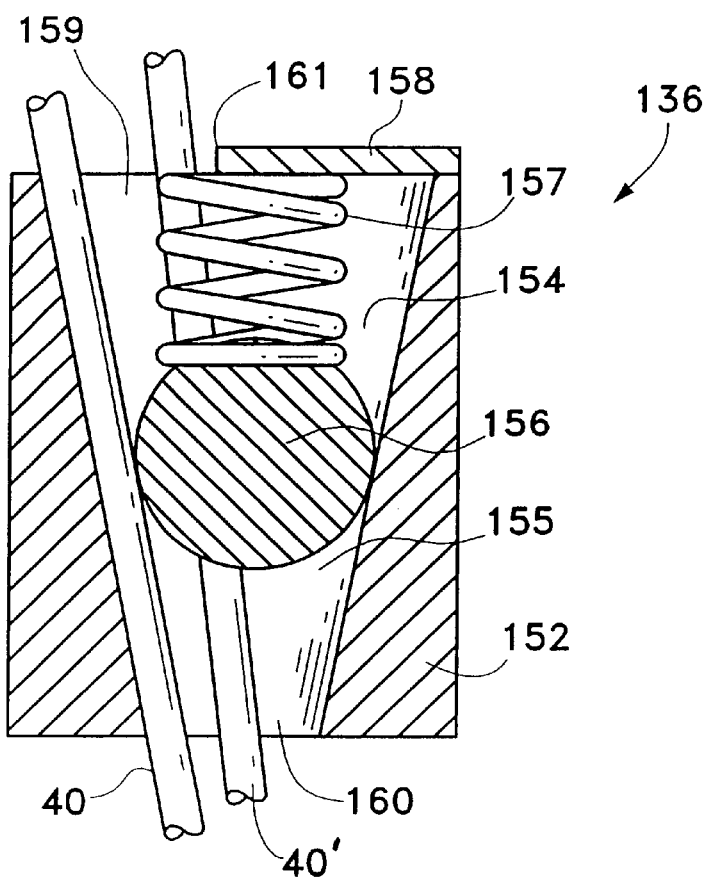
FIG. 18 is a side cross sectional view of the self-locking device of FIG. 17 taken along the line 18—18 of FIG. 17.

FIGS. 17 and 18 illustrate one embodiment of the connection device 36. The self-locking device 136 is configured to permit each of the cords 40, 40' to traverse away from the self-locking device in a direction toward the free ends 41, 41'. The connection device 136 may also be configured to prevent each of the cords 40, 40' from traversing away from the self-locking device in a direction toward the attached ends 43, 43' of the cords 40, 40'. The self-locking device 136 includes a passageway or channel 155 extending through the self-locking device 136, from a first opening 159 to a second opening 160. The cords 40, 40' pass through the openings 159, 160 and hence through the channel 155 in the self-locking device 136. The self-locking device 136 prevents the cords 40, 40' from being pulled back toward the anchors 38, 38'. When the self-locking device is located in the lung, it only permits the portion of the cords 40, 40' in the channel 155 to travel or be displaced relative to the self-locking device in a direction toward the trachea, not toward the outer periphery of the bronchial tree where the anchors 38, 38' are located.

In general, the self-locking device 136 allows the cords 40, 40' to pass in one direction, but locks the cords in place when they are forced to move the in the other direction. This variation of the self-locking device 136 may include a cylindrical body 152 having a tapered inner wall 154 that extends through the body 152 to define the conical channel 155. Thus, as shown in FIG. 18, the tapered inner bore 154 defines a conical interior. A ball 156 rests in the channel 155 and is retained therein by a cap or cover 158 located over the larger end of the taper. The cover 158 preferably covers the larger end of the bore to such an extent that the area of the first opening 159 is smaller that the cross-sectional area of the ball 156. However, the opening 159 should be large enough to permit at least one line 40 to pass through the first opening. In the embodiment illustrated in FIG. 18, the first opening 159 is large enough to permit two cords 40, 40' to pass there-through. Because the cover 158 does not completely cover the larger bore diameter of the conical channel 155, the cords 40, 40' will fit through the gap or first opening 159 between the wall 154 and the edge 161 of the cover 158. Thus, the cords 40, 40' fit through the gap 159. Other embodiments of the self-locking device 136 may be configured to receive more than two cords.

The self-locking device 136 is dimensioned and configured such that when a cord 40 is pushed or pulled through the smaller second opening 160 (or smaller bore), the cord 40 will displace the ball 156 toward the cap 158 just enough for the line to continuously pass through the self locking device. When the line 40 is pushed or pulled in the opposite direction, the ball 156 will displace towards the smaller second opening 160, i.e., away from the cap 158. Because the ball 156 has a larger cross-sectional area than that of the smaller second opening 160, the ball will wedge against the conical inner wall 155 and the cord 40, locking, wedging, or chocking the cord in place. For example, if the cord 40 is pulled toward the cover 158, the self-locking device 136 will permit the line to be pulled in this direction. However, if the line 40 is pulled in the opposite direction away from the cover 158, the ball 156 will wedge against the line 40 and the inner wall 154 such that the line 40 cannot travel relative to the self-locking device 136. This wedging effect occurs because of the friction between the ball 156, the line 40, and the wall 154. Additionally, the self-locking device may be configured with a spring 157, such as a coil or leaf spring, that may be positioned between the cover 158 and the ball 156 to ensure that the ball is always biased towards the small opening 160 of the device.

As described above, and as shown in FIG. 18, the self-locking device 136 is configured for two cords 40, 40'. The self-locking device 136 will self-lock two cords 40, 40' and only permit the lines 40, 40' to be moved in the direction toward the cover 158. When the self-locking device 136 is used in the present invention, the direction toward the cover 158 is also the direction towards the trachea, away from the position where the self-locking device is located. Although the function of the self locking device 136 has been described in reference to the cords 40, 40' being pushed or pulled, it should be recognized that the self-locking device at least permits one way movement of the chords so that the distance between anchors may be reduced.

Although the self-locking device 136 illustrated in FIGS. 17 and 18 is the preferred embodiment of the connection device 36, other connection devices that have a locking, chocking, or wedging function are contemplated. For example, a connection device may include a plurality of tapered inner bores 154 and balls 156 each configured to receive and lock one line 40, rather than two lines 40, 40'. Additionally, other self-locking, chocking, cleating, or wedging devices such as devices similar to those used on sailing and marine vessels would also perform adequately. Also, clasping, clamping, or even gluing or melting the lines together may suffice as a connecting device 136.

Furthermore, as described earlier, the connection device 36 need not have a self-locking function. The connection device 36 need only substantially prevent the first cord length (measured between the first anchor 38 and the connection device 36) and the second cord length (measured between the second anchor 38' and the connection device 36) from increasing. This result occurs because the connection device 36 does not allow relative movement between connected cords 40, 40' with respect to the connection device when the connection device connects or fixes together the cords 40, 40'. Hence, after the cords 40, 40' have been connected and when the first cord 40 is forced in a state of -tension or is pulled, the second cord 40' will also be forced in a state of tension or will be pulled. As described earlier, the connection device 36 can also function as an anchor, or the anchor 38 can function as a connection device. For example, the self-locking device 136 can include a plurality of barbs or hooks such that it can be anchored to a bronchial passageway or a bifurcation between two airways.

Referring again to FIGS. 10–13, after the anchors 38, 38' have been fixed or lodged in different positions in the bronchial tree, the cords 40, 40' can be tensioned. FIGS. 10–13 illustrate how the anchors 38, 38' may be used to collapse the tissue of the lung to decrease the volume of the lung. As described earlier, the anchors 38, 38' may be lodged in the outer periphery or most distal part of the bronchial tree through a delivery device 34 or a standard bronchoscope inserted through the mouth or nose of the patient. After the anchors 38, 38' are in place, the cords 40, 40' are gathered together and the free ends 41, 41' are inserted through the connection device 36 and then into the first end 37 of the delivery device 34, which may be the same delivery device that was used to deliver the anchors 38, 38', or a different delivery device. The gathered cords 40, 40' are received by the delivery device 34 until the free ends 41, 41' protrude from the second end 39 of the delivery device 34. The first end 37 of the delivery device 34 along with the connection device 36 is then inserted into the trachea and into the bronchial tree towards the lodged anchors 38, 38'. FIG. 11 illustrates the delivery device 34 first entering the bronchial tree. FIG. 12 illustrates the delivery device 34 positioned farther into the bronchial tree towards the anchors 38, 38'. The free ends 41, 41' are preferably prevented from entering the lung while the delivery device 34 is being inserted into the lung with the cords 40, 40' therein. At this point in time, as illustrated by FIGS. 11 and 12, the lung has not been collapsed and is in its original position A.

Then, as illustrated in FIG. 13, at least one of the cords 40, 40' is pulled in tension such that the distance between the first anchor 38 and the second anchor 38' ("the anchor distance $L_{AD}$") decreases; this decrease in distance between the lodged anchors is what causes the volume of the lung to decrease. The more the anchors 38, 38' are drawn toward each other, the more the volume of the lung will decrease. By tensioning the lines 40, 40' the anchors 38, 38' will pull on the lung tissue in the direction toward the median between the anchors. The more the anchor distance $L_{AD}$ decreases, the more the lung tissue will collapse to decrease the volume of the lung. However, because the lung is generally elastic and will strive to return to its original position, it is necessary to maintain the decreased anchor distance $L_{AD}$ with the connection device 36 by connecting the cords 40, 40' to each other before the anchors have the opportunity to return to their original position. The connection device 36 connects the cords 40, 40' such that the reduced anchor distance $L_{AD}$ is maintained. Once the cords 40, 40' are connected by the connection device 36 and the reduced anchor distance is maintained, the cords 40, 40' will remain in tension due to the elastic properties of the lung. As shown in FIG. 13, the lung tissue has been partially collapsed or compressed to the new position B from the original position A. Thus, the volume of a portion of the lung has been compressed or decreased in accordance with one embodiment of the present invention.

The delivery device 34, or another similar device, can be used to locate or position the connection device 36 into the interior of the lung along the bronchial tree toward the anchors 38, 38'; this can occur before, during, or after the anchor distance $L_{AD}$ has been decreased. After the anchor distance $L_{AD}$ has been decreased by pulling the anchors 38, 38' towards one another via at least one of the cords 40, 40', the connection device 36 connects the cords such that the anchor distance $L_{AD}$ is maintained and the lung volume remains reduced. Thereafter, the portions of the cords 40, 40' between the connection device 36 and the free ends 41, 41' are cut or broken from the tensioned portions of the cords 40, 40' that maintain the reduced anchor distance LAD. The cut portion of the cords 40, 40' having the free ends 41, 41' is removed from the reduced volume lung. The delivery device 34 is also removed from the reduced volume lung. The cords 40, 40' can be cut by a variety of techniques well known in the art. The anchors 38, 38', spaced from each other by the reduced anchor distance $L_{AD}$, and the tensioned cords 40, 40' remain in the reduced volume lung, preferably for the life of the patient.

FIG. 10 illustrates how the preferred self-locking device 136 connects cords 40, 40' together. Although not illustrated, a second anchor 38' has been secured to the bronchial passageway at a place distant from that where the first anchor 38 is positioned. The second line 40' is attached to the second anchor 38'.

As shown in FIGS. 10–13, the delivery device 34 may be used to force the self-locking device 136 towards the anchors 38, 38' to pull the anchors via the cords 40, 40'. The self locking device 136 may also be released from the inside of the delivery device 34, or from the working channel of a standard bronchoscope. Because the free ends 41. 41' of the cords 40, 40' are held taut, as the self-locking device 136 is moved toward the anchors 38, 38', the cords 40, 40' move relative to the self-locking device. As the self-locking device 136 is moved closer and closer to the anchors 38, 38, the cords 40, 40' can be pulled or further tensioned to reduce the anchor distance $L_{AD}$.

As shown in FIG. 10, and as described earlier in greater detail, the self-locking device or chock device 136 cinches-up on the cords 40, 40' and holds them in place while they are pulled and/or while the self-locking device is pushed toward the anchors. Because the self-locking device 136 automatically prevents the cords 40, 40' from reversing direction back toward the anchors 38, 38', once the desired reduced anchor distance $L_{AD}$ is obtained, the self-locking device 136 automatically connects the cords 40, 40' to each other such that the reduced anchor distance $L_{AD}$ is maintained. Thus, there is no need to manually connect the cords 40, 40' to each other with a clasp or other connecting device 36. The more the anchors 38, 38' are pulled toward the self-locking device 136 (generally located at the median between the anchors) via the lines 40, 40', the more the lung tissue will collapse inward.

Although only two anchors are illustrated in FIGS. 11–13, more anchors can be used to further collapse or compress the volume of a portion of the lung. For example, three anchors may be spaced approximately 120 degrees apart from each other such that the anchors 38 each tension an equal portion of the area to be collapsed. In this manner, a larger portion of the lung may be collapsed, thus reducing the volume of the lung to a greater extent.

Additionally, as illustrated in FIGS. 19 and 20, the distance between two anchors 38, 38' can be decreased by pulling or tensioning one cord 40, rather than two cords. For example, the first anchor 38 can be anchored or fixed at a first location and a second anchor 38' is fixed or located at a second location. The first anchor 38 and the second anchor 38' are separated by an original distance $L_{OD}$. The cord 40 is attached to the anchor 38 before it has bee n anchored. Alternatively, the cord 40 can be attached to the first anchor 38 after the anchor 38 has been anchored at the first position. In FIG. 19, the cord 40 is slack or limp, and the anchors 38, 38' are in their original positions.

As illustrated by FIG. 20, the cord 40 is pulled to decrease the distance between the anchors 38, 38' or move one anchor 38 toward the other anchor 38'. The cord 40 is placed in tension to pull the anchor 38 toward the anchor 38' to defined the anchor distance $L_{AD}$ which is less than the original distance $L_{OD}$. Thereafter, the tensioned cord 40 can be attached to the second anchor 38' such that the distance between the first anchor 38 and the second anchor 38' is not permitted to return to the original distance. The remaining non-functional portion of the cord 40 has been removed by cutting the cord 40 at a location directly adjacent to the anchor 38 and then pulling the excess cord from the lung. As shown in FIGS. 19 and 20, the second anchor 38' is a self-locking device, such as that shown in FIGS. 17 and 18, but has barbs or hooks such that it also is an anchor. Thus, the distance between the two anchored anchors 38, 38' can be reduced by pulling one cord 40 to compress the volume of a portion of the lung.

Furthermore, the cords can be an elastic device that regains its original shape after compression or extension, such as a coil of wire that keeps anchors attached thereto under constant tension. The cord can provide a constant or discontinuous tensile force to the anchors. For example, the cord can be an elastic filament such as a rubber band, or a expandable spring.

The connection device 36, 136 and its components, the anchor 38, 138, and the line 40 may be made from a chemically inert and biocompatible, natural, or synthetic material which is well known in the art. Such material is preferably a non-bioerodable material which will remain in the patient after use, such as titanium or a titanium alloy. Generally, preferred materials are those acceptable for human implants. In general, typical materials of construction suitable for the above-mentioned items include non-reactive polymers or biocompatible metals or alloys. Metallic materials useful include stainless steel, platinum, tantalum, gold, and their-alloys, as well as gold-plated ferrous alloys, platinum-plated ferrous alloys, cobalt-chromium alloys, nickel titanium alloys, and titanium nitride coated stainless steel. For example, the cables can be made from nylon, and the anchors can be made from a titanium alloy. The cables can be made from elastic materials such as an elastomer that is stretchable like a rubber band.

FIGS. 21A–29 illustrate further variations of an anchor of the present invention. It is intended that the drawings not limit the physical attributes of the anchors illustrated. For example, it is contemplated that the anchors may have more or less tines than shown by the drawings. Moreover, the ends of the attachment portion may be selected to be atraumatic to the walls of the airway or may be selected to penetrate the walls of an airway. One variation of the anchor includes anchors that are sized to enter airways of less than 3 mm in approximate diameter.

FIG. 21A illustrates an anchor 170 having a central portion 176 and an attachment portion 174. In this view, the attachment portion 174 of the anchor 170 is in a reduced profile. This profile is preferably sized such that the anchor 170 may be advanced through airways of the lung. As shown in FIG. 21A, the anchor 170 may additionally have a cord 172 extending from the central portion 176. FIG. 21B is a rear view of FIG. 21A taken along the line 21B in FIG. 21A. In this variation of the anchor, the anchor 170 is illustrated to have four tines 174 which comprise the attachment portion. However, it is contemplated that the number of tines 174 may vary as desired or needed. FIG. 21C illustrates the anchor 170 of FIG. 21A with the attachment portion or tines 174 in an expanded profile. Preferably, the expanded profile is sized such that the anchor 170 will attach to a wall of an airway or other lung tissue. As noted below, the attachment portion 174 of the anchor 170 may provide a frictional hold against the airway walls which may include a deformation of the airway walls or the attachment portion 174 may penetrate the airway walls. FIG. 21D is a rear view of FIG. 21C taken along the line 21D. The attachment portion 174 of the anchor 170 may be mechanically deformable to attain the expanded profile, or it may be restrained into the reduced profile whereupon the removal of the restraint causes the attachment portion 174 to expand into the expanded profile. Also contemplated is the use of a shape memory alloy which allows the attachment portion 174 to assume the expanded profile by a change in temperature.

Figure 22A:
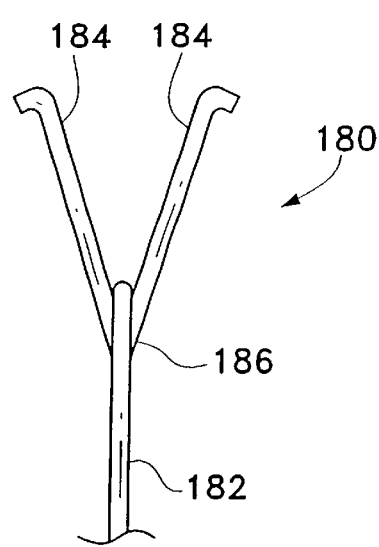
Figure 22B:
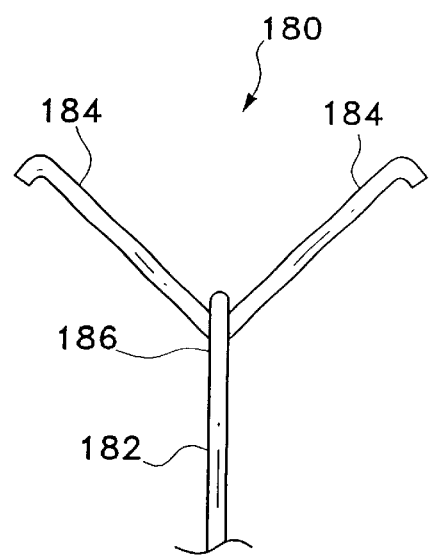

FIGS. 22A–22B illustrate another variation of an anchor 180. In this variation, the anchor is shown to have an attachment portion comprising two tines 184. The tines extend from the central portion 186 to which the cord 182 is attached. In this view, the anchor 180 is in a reduced profile. FIG. 22B illustrates the tines 184 of the anchor 180 in an expanded profile. As noted above, the tines 184 may assume an expanded profile through mechanical deformation. Or, the tines 184 may be restrained in a reduced profile whereupon removal of the restrain causes the tines 184 to self-assume the expanded profile.

Figure 23A:
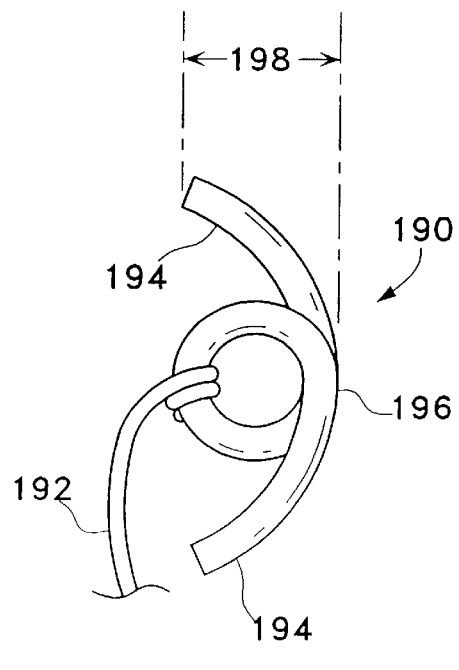
Figure 23B:
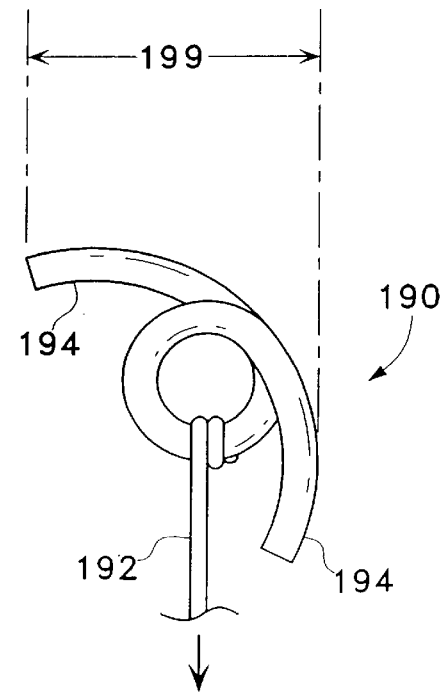

FIGS. 23A–23B illustrate another variation of an anchor 190. In this variation, the anchor 190 may comprise a wire having a central portion 196 and ends which comprise the attachment portion or tines 194. A cord 192 may be attached to the central portion 196. FIG. 23A illustrates the anchor having a reduced profile as measured by a width 198 comprising the distance from the tines to the central portion. This width 198 is preferably selected such that the anchor 190 may be advanced into an airway of a lung using a delivery device of some kind. FIG. 23B illustrates the anchor 190 having been rotated such that a width 199 is larger than the width 198. The anchor 190 may be rotated by placing the cord 192 in tension within an airway wall. It is contemplated that rotation of the anchor 190 in an airway causes the tines 194 of the anchor to attach to the walls of the airway.

Figures 24A, 24B:
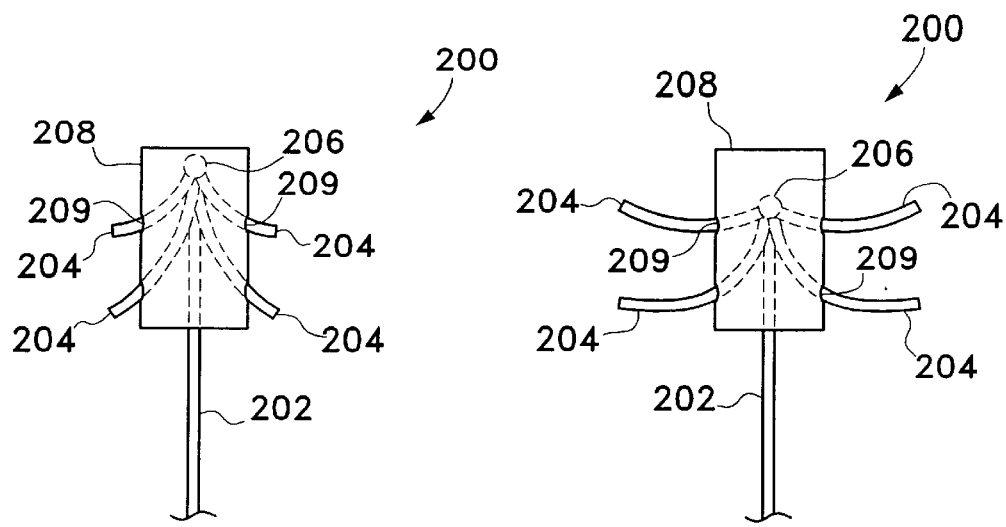

FIGS. 24A–24B illustrate another variation of an anchor 200. In this variation, the anchor may have a covering 208 having a wall with openings 209. The anchor 200 has a central portion 206 and an attachment portion or tines 204. In the illustration of FIG. 24A the tines 204 of the anchor 200 are in a reduced profile. FIG. 24B illustrates the anchor 200 with the tines 204 in an expanded profile. The tines 204 of the anchor 200 may be moved into the expanded profile by moving the cord 202 in a direction away from the anchor 200 as illustrated by the arrow in FIG. 24B.

Figures 25A, 25B:
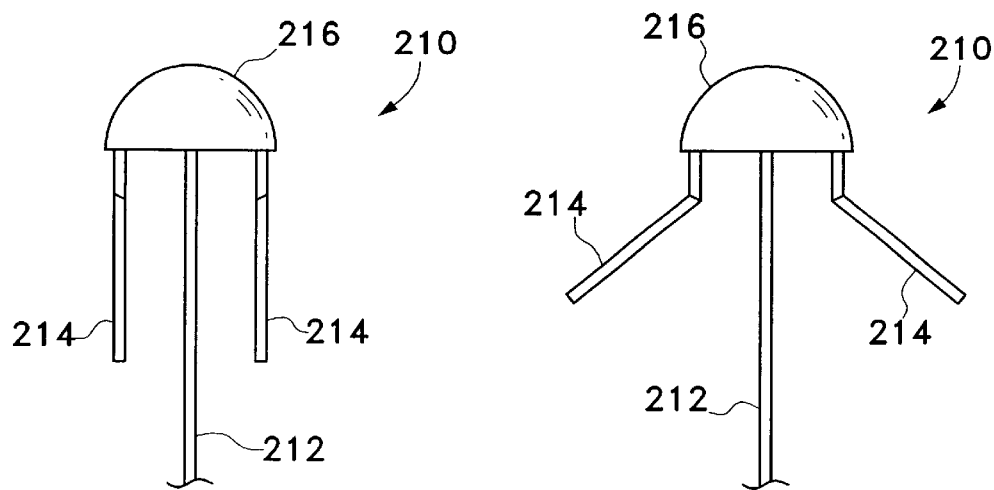

FIGS. 25A–25B illustrates yet another variation of an anchor 210 having a central portion 216 and an attachment portion or tines 214 and a cord 212 attached to the central portion. FIG. 25A illustrates the anchor 210 in a reduced profile while FIG. 25B illustrates the anchor 210 with the tines 214 in an expanded profile.

Figures 26A, 26B:
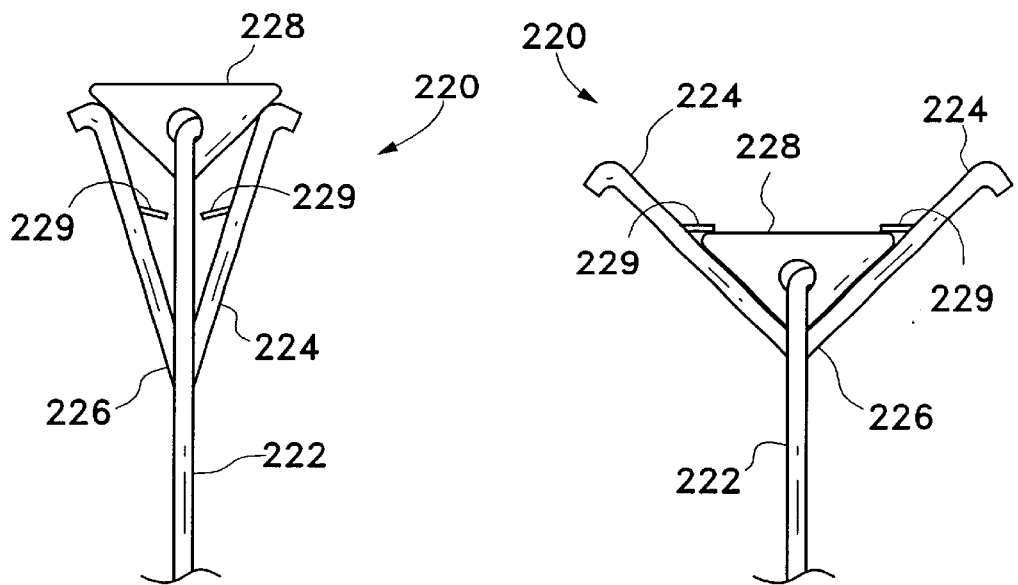

FIGS. 26A–26B illustrates another variation of an anchor 200 wherein a cord 222 has a wedge 228 that may be attached at a distal end of the cord 222. FIG. 26A illustrates the anchor 220 where the tines 224 are in a reduced profile as the wedge 228 is at an end of the anchor 220. FIG. 26B illustrates the wedge 228 as having been moved towards a central portion 226 of the anchor wherein the wedge 228 forces the tines 224 to assume an expanded profile. The anchor 220 may have stops 229 to retain the wedge 228 as illustrated in FIG. 26B.

Figures 27A, 27B:
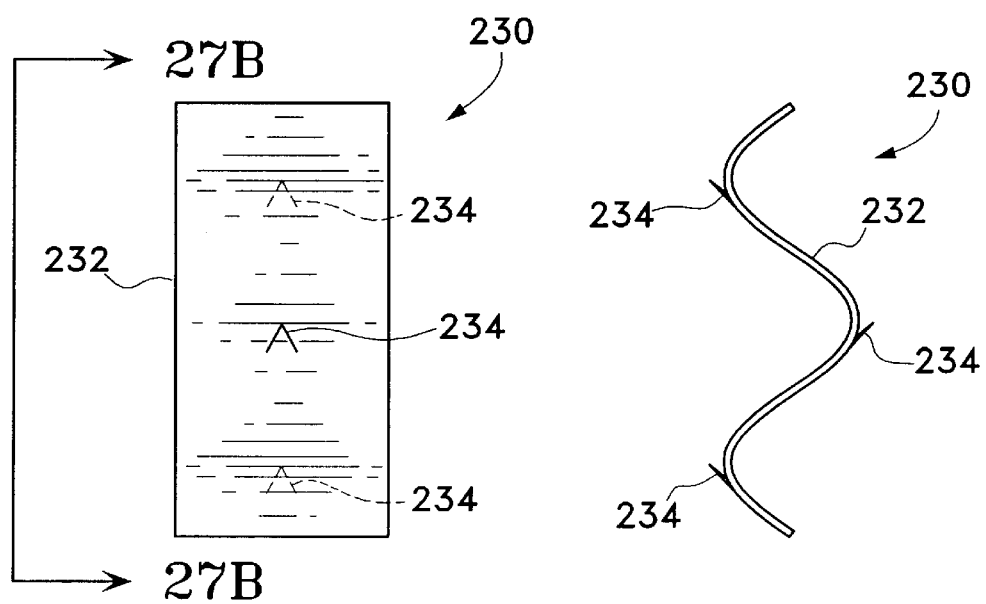

FIGS. 27A–27B illustrates another variation of an anchor 230. FIG. 27A shows the anchor 230 as having a body comprising a flat spring 232. The anchor has attachment portion or tines 234 extending away from the body 232. FIG. 27B shows a side view of the anchor 230 as taken along the line 27B in FIG. 27A.

FIGS. 28–29 are intended to illustrate anchors 236, 242 having a fibrosing agent 240, 244 placed in proximity to the tines 238, 245. The fibrosing agent is intended to be an irritant that induces fibrosis of tissue that assists the anchor in adhering to the lung. Also, the fibrosing agent may strengthen the tissue surrounding the anchor thus preventing the anchor from tearing the tissue. An example of a fibrosing agent is powdered talc or a slurry composed of powdered talc and water or saline. However, fibrosing agents can be composed of any biocompatible agent that at least produces a degree of tissue irritation. The fibrosing agent may be applied to an anchor by any process, including but not limited to, brushing, dipping, spraying, coating or a combination thereof. FIG. 28 illustrates the fibrosing agent 240 as a solid form, however, the agent may also be powdered. The agent may be in a solid form that is crushed into a powder as the anchor assumes an expanded profile.

FIG. 30 illustrates a variation of a delivery device 246 used for placing an anchor at a site within the lungs. In this variation, the delivery device 246 has a lumen 256 extending through the device 246 and a seal 252 at within the lumen 256. The delivery device 246 also has a fluid delivery port 254 for allowing fluid to be delivered through the device 246. The port 254 may have a luer fitting to facilitate joining the port 254 with a source of the fluid. The seal 252 preferably allows the cord 250 to exit from the proximal end of the delivery device 246. One intended use for the device is to deliver a fibrosing liquid or slurry through the device 246 to a site at which an anchor is located within the lungs. As mentioned above, the fibrosing liquid is intended to be an irritant that produces fibrosis of tissue at the site of the anchor. The production of the fibrotic tissue assists the anchor in remaining at the desired position and anchored to the desired tissue in the lung.

FIGS. 31A–31B illustrate another variation of a delivery device 260. As shown in FIG. 31A, the delivery device 260 has openings 264 which permit the anchor 262 to expand out of the delivery device 260. As shown in FIG. 31B tines 266 of the anchor 262 extend through the openings 264 of the delivery device 260 as the tines 266 expand to assume an expanded profile.

Figure 32A:
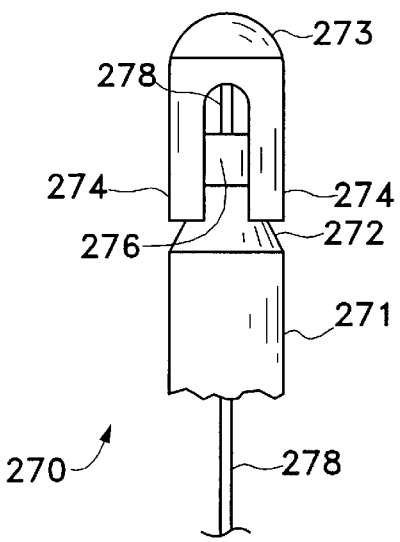
Figure 32B:
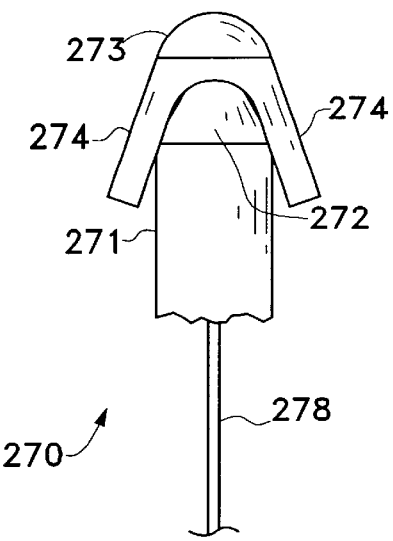

FIGS. 32A–32B illustrate another variation of a delivery device 270. FIG. 32A shows the delivery device 270 with an anchor 273 removably seated on a tapered section 272. A cord 278 extends from the anchor 273 through the body of the device 271 and out of the proximal end of the device. By extending out of the device 270, the cord 278 may be pulled in a proximal direction to allow the tines 274 of the anchor 273 to expand. FIG. 32B illustrates the expansion of the tines 274 to assume an expanded profile as the tines 274 are mechanically deformed by the tapered section 272 of the delivery device 270. As shown in FIG. 32A the delivery device may also have a guide section 276 which directs the anchor 273 as it is pulled over the tapered section 272.

Figure 33A:
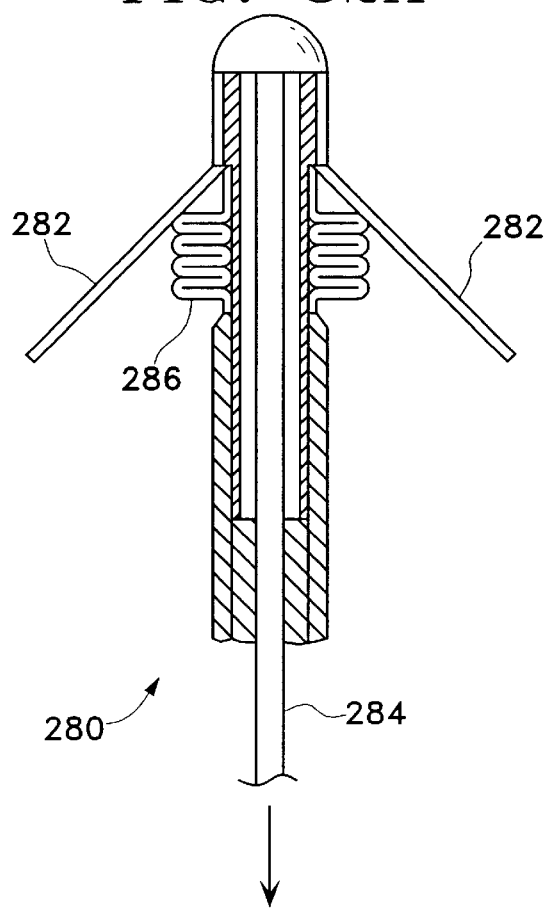
Figure 33B:
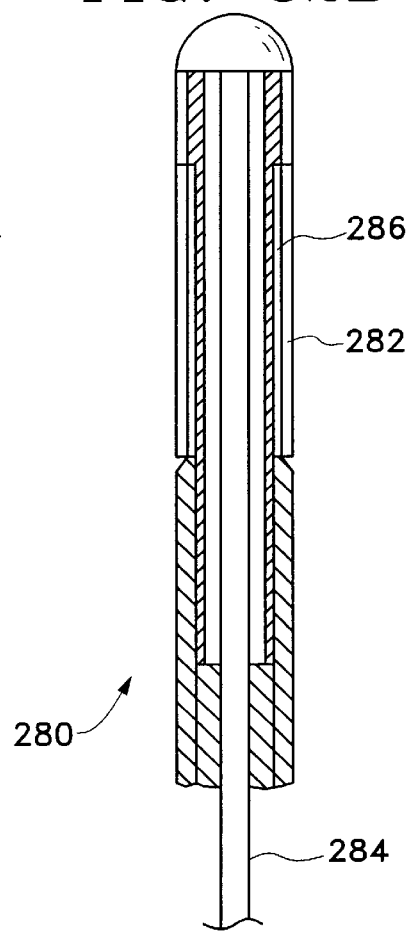

FIGS. 33A–33B illustrate another variation of a delivery device 280. As shown in FIG. 33A, the delivery device 280 has a compressible sleeve 286 in contact with the tines 282 of the anchor. As shown in FIG. 33B, as the cord 284 of the anchor is pulled in a proximal direction, the compressible sleeve 286 expands in diameter forcing the tines 282 to assume an expanded profile.

FIGS. 34A–44 illustrate variations of the connection device (hereafter variously referred to as connector, connection device, or self-locking device) for use with this invention. It is intended that the drawings not limit the physical attributes of the illustrated connectors. For example, the connectors may be used with any number of cords. The bodies of the connectors may be rigid or elastic as required. The connectors serve to connect multiple anchors having cords. Therefore, as the cords are placed within the lungs and are adjusted to compress the lung tissue, the connectors shall prevent movement of the cord to prevent maintain compression of the lung tissue.

FIGS. 34A–34B illustrate cross sections of variations of a connector 300. In this variation, the connector 300 comprises a simple body 304 having a passageway 302. The connector 300 may be cylindrical or non-cylindrical cross section. In one variation, as shown in FIG. 34B, a connector 300 may comprise the body 304 with a reduced diameter 306 of the passageway 302. The reduced diameter 306 may be obtained by crimping or bending the body 306 of the connector 300. The reduced diameter 306 provides a stop that prevents movement of a cord of an anchor (not shown) after the cord (not shown) is advanced to a desired location.

FIG. 35 illustrates a cross section of another variation of a connector 310. In this variation, the connector has body 312 having a passageway 313, and a plug 316 which seats into a ring 314. In this variation, a cord (not shown) is inserted into the body 312 of the connector 310 through the passageway 313 and through the ring 314. Insertion of the plug 316 into the ring 314 prevents movement of the cord (not shown.) The plug 316 may be formed of a resilient material and the ring 314 may be formed from a rigid material to allow for secure placement within the ring 314.

FIGS. 36A–36B illustrates cross sections of a variation of the connector 320 having a plurality of stops 324 within a body 326 of the connector. FIG. 36A illustrates a variation of the invention in which, the connector 320 includes a tube 322 inserted through the passageway. A cord (not shown) is inserted through the tube 324. Upon movement of the cord to a desired position, the tube 322 is removed from the connector body 326 which permits the stops 324 to provide frictional resistance against the cord (not shown) thereby preventing movement of the cord. The body 326 of the connector 320 may be elastic to provide an additional force against the stops to provide additional frictional forces which prevent movement of the cords. FIG. 36B illustrates the connector 320 of FIG. 36A in which the tube (not shown) is removed leaving a cord 323 within the connector 320. The stops 324 provide resistance sufficient to prevent the cord 323 from moving.

FIG. 37A illustrates cross section of a variation of a connector 330 having a body 338 with a passageway 336 extending through the body 338. This variation of the connector also has a moveable section 332 within the body 338. The moveable section 332 has a hole 331 that may be aligned with the passageway 336 thereby allowing the placement of a cord (not shown) through the passageway 336. As shown in FIG. 37A, when the hole 331 of the moveable section 332 is offset from the passageway 336, the cord (not shown) will be prevented from moving. In this variation, the stop of the connector comprises the moveable section 332. The moveable section may be, but is not necessarily, spring biased to assume a nonaligned position with the passageway 336.

FIG. 37B shows a cross section of a variation of the connector 330 of FIG. 37A. In this variation, a tube 339 is used to keep the moveable section 332 in alignment with the passageway 336. A cord (not shown) is placed through the tube 339. Upon the desired placement of the cord relative to the connector 330, the tube 339 is removed allowing the moveable section 332 to hold the cord (not shown) within the connector 330.

FIG. 38 illustrates a cross section of another variation of a connector 340. In this variation, the connector has a body 344 with a passageway 349 having a reduced diameter 346. A stop in the form of a plug 342 is inserted into the section of reduced diameter 346 for providing resistance against a cord 348 to prevent movement of the cord 348. Although the plug 342 is depicted as being spherical it is not limited as such. The plug 342 may be rectangular or wedge-like with the purpose of fitting within the reduced diameter section 346 of the connector 340. Also, the reduced section of the connector may be configured to mate with the particular design of the stop. Another variation of the connector includes a single connector body having multiple passageways each with reduced diameters and having multiple stops within the passageways. This variation allows several anchors to be joined together but only one cord per passageway. A preferred variation of this invention is having six passageways, each of which has a plug.

FIG. 39 depicts a cross section of another variation of a connector 350 comprising a body 354 having a passageway 356 with a plurality of prongs, flaps, or fingers 352 extending away from the body 354 towards the center of the passageway 356. The prongs 352 may be used to prevent the movement of a cord having a hook or loop at a proximal end of the chord (not shown). The prongs may be comprised of a resilient material or they may be fabricated to allow flexing. In another variation, the prongs may be angled towards an open end of the connector. In such a variation, when a cord is drawn through the connector in the direction of the angled prongs, the cord will slide freely. When the cord is moved in the opposite direction, the angle of the prongs and the frictional forces between the cord and the tip of the prongs causes the tips of the prongs to wedge into the side of the cord and prevent the cord from sliding in the opposite direction.

FIG. 40A illustrates a cross section of a connector 360 having a stopper 364 located within a passageway 369 of the connector 360. The passageway 369 allows for passage of a cord 370 through the connector 360 with the stopper 364 preventing movement of the cord 370. The stopper 364 may be comprised of an elastomeric material or may be a rigid material. The stopper 364 may be attached to a body 362 of the connector 360 by a spring element 366. The spring element 366 may comprise an elastomeric material, such as the case where the stopper 364 and the spring element 366 are a continuous piece. Or, the spring element 366 may comprise a coiled or other type of spring. FIG. 40B illustrates the connector 360 of FIG. 40A as the stopper 364 is pulled through the passageway 369 to permit passage of a cord 360 having a section of increased diameter as the cord is pulled through the connector. Both FIGS. 40A and 40B illustrate the stopper 364 on the connector 360 as having a plug 368. The plug 368 may be used to pull the stopper 364 out of the passageway 369 after the cord has been attached to the connector 360. This feature allows one to release the cords from the connector 360.

FIG. 41 illustrates another variation of a connector 372 having a stopper 374 attached to a base 376 of the connector 372. In this variation, the base 376 serves as a spring element for the connector 372.

Apart from the connectors described above, it is contemplated that the connector comprise an adhesive to join multiple cords together. The cords may also be simply tied together.

Figure 42A:
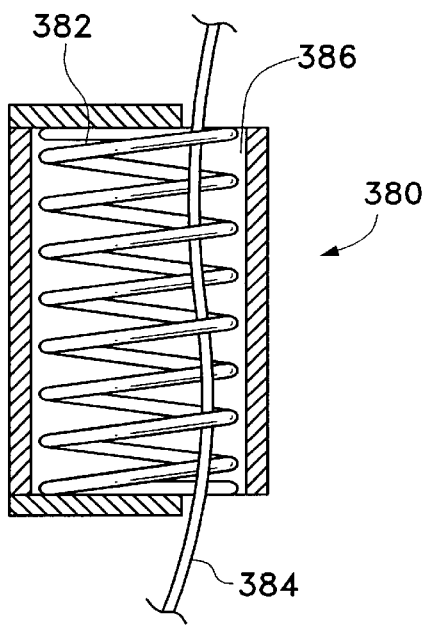
Figure 42B:
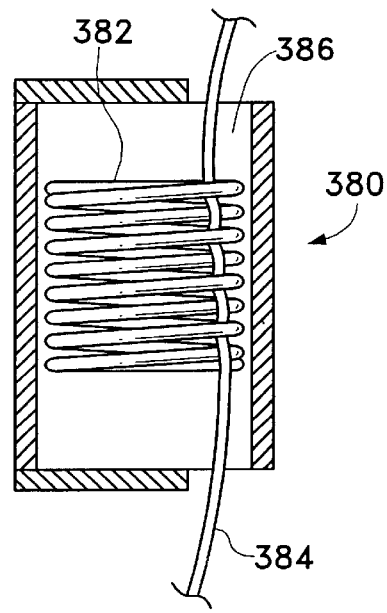

FIGS. 42A–42B illustrate cross sectional views of a connector having a passageway 386 with a spring 382 having a plurality of turns through which a cord 384 is woven. As illustrated in FIG. 42A the spring 382 is stretched to permit movement of the cord. FIG. 42B illustrates the spring 382 returning to its natural state whereby compression of the turns of the spring 382 prevents movement of the cord 384.

Figure 43A:
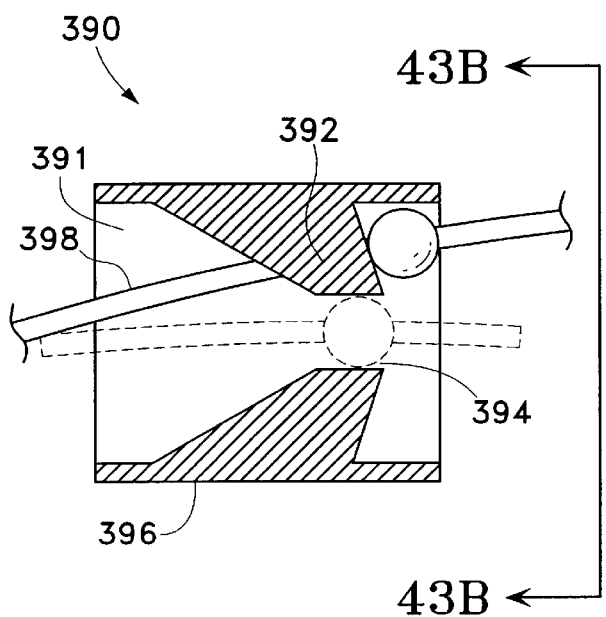
Figure 43B:
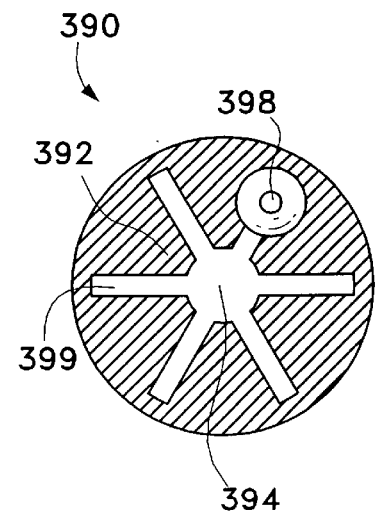

FIG. 43A illustrates a cross sectional view of a connector 390 having a body 396 having a passageway 391 with a flange 392 having a central opening 394 with a plurality of slots 399 extending from the central opening. As illustrated in FIG. 43A a cord 398 having a section of increased diameter is pulled through the central opening 394 and nested in a slot 399. FIG. 43B illustrates the nesting of a cord 398 in a slot 399 in the connector 390.

FIG. 44 illustrates another variation of a connector 400 having a body 406 having a passageway 404 with a section of reduced diameter 401 in which may be seated a plug 402. A cord (not shown) may be inserted through the passageway 404 and through the section of reduced diameter 401, wherein movement of the cord is prevented by insertion of the plug 402 into the section of reduced diameter 401. FIG. 45A illustrates a side view of a plug 402. FIG. 45B illustrates a top view of the plug 402. The plug may have a slot 408 which assists in insertion of the plug 402 into the section of reduced diameter 401. Although FIG. 44 illustrates the connector as having three plugs 402 and three sections of reduced diameter, the connector 400 is not limited as such. For example, the connector 400 may have up to six plugs and six sections of reduced diameter for insertion and retention of six chords.

FIG. 46 illustrates a variation of an anchor device 410. In this variation, the anchor device 410 has a central portion 412 an attachment portion 414 and a cord 418 that may extend from the central portion 412. This variation of the anchor 410 has a cord 418 which has segments 416 of increased diameter. Although these segments 416 are depicted as being spherical they are not limited as such and may be of any shape so long as they have a greater dimension than the cord. The segments 416 may be adjustable on the cord 418 thereby allowing effective adjustment of the length from the placement site of the anchor in the lung to a connector. This variation of the anchor device 410 may be used with a simple tubular connector (not shown) with another similar anchor device wherein the anchor devices are placed in tension in opposite directions and the sections of increased diameter provide interference within the tube preventing movement of the cords.

FIG. 47 illustrates a variation of a cord 420 for use with the invention. In this variation, the cord 420 comprises a tube 422 having a lumen 424. The tube 422 may be elastic. The lumen 424 allows for assisting in ventilation of air between portions of the lungs that are compressed by the assembly of the invention described herein. As shown in FIG. 47, the chord 420 may have openings 426 in the lumens to assist in the transportation of air. The use of an elastic tube may further assist in collapsing or reducing the section of lung between the anchors.

FIG. 48 illustrates another variation of an anchor device 430 with the cord 436 having a hook 438 at a proximal end of the cord 438. In this variation, the hook 438 may simply attach to an end of a tubular connector (not shown). It is also contemplated that instead of the hook 438, the cord may have a loop or ring so that the cord may be secured to a connector. FIG. 48 also illustrates a variation of the invention in which the anchor 432 is attached to a hook 438 via an elastic cord 436. In such a case, the hook 438 may adhere to a portion of the lung and the anchor may adhere to a second distant portion by stretching of the cord 436. The anchor 432 will be drawn towards the hook 438 as the cord 436 returns to its relaxed state. This variation of the anchoring device 430 may eliminate the need for a connector (not shown).

FIGS. 49–53 illustrate variations of cutters for use with the invention described herein. The cutters trim the excess cord after the anchor is set and the cords are pulled to collapse the volume of lung tissue.

Figure 49:
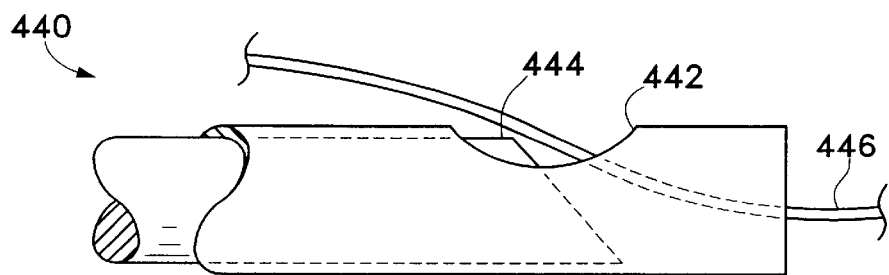
FIGS. 49–53 illustrate variations of the cord cutter of the present invention.

FIG. 49 illustrates a variation of a cutter 440 having an elongate member 443 having a first shearing surface 442 and a second shearing surface 444 within the elongate member 442. As the first shearing surface 442 and the second shearing surface meet, the cord 446 is cut.

Figure 50:
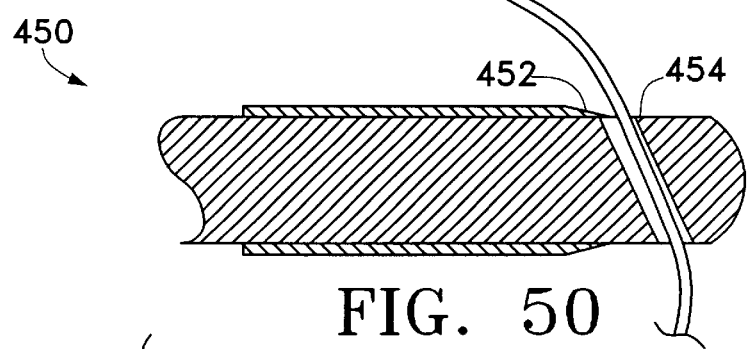

FIG. 50 shows a cross section of a variation of a cutter 450 where a shearing surface 452 cuts a cord 446 as it joins a second shearing surface 454.

Figure 51:
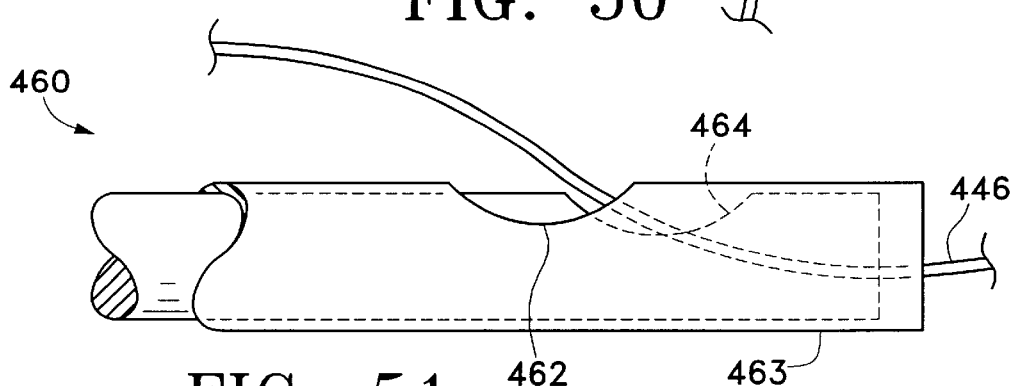

FIG. 51 illustrates another variation of a cutter 460, in this variation an elongate member 463 has a first shearing surface 462 while a second shearing surface 464 is moveable within the elongate member 463. The second shearing surface 464 may be axially moveable within the elongate member or torsionally moveable or a combination thereof.

Figure 52:
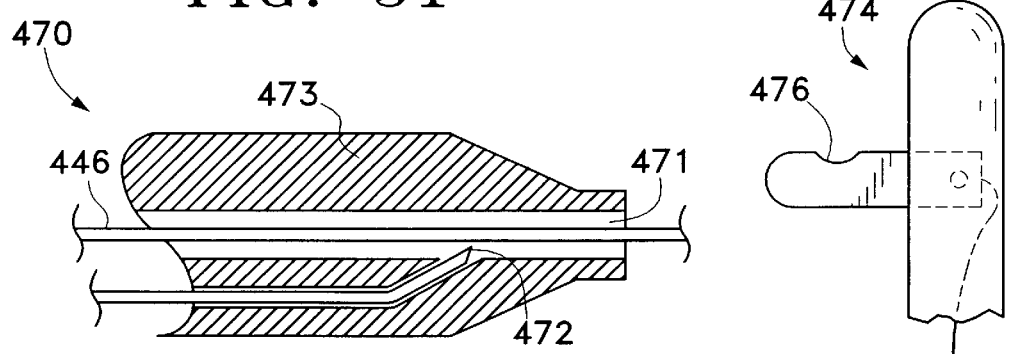

FIG. 52 illustrates a variation of a cutter 470 wherein a cutter 472 extends into a passageway 471 of a delivery device 473 to cut a cord 446. In this variation, the cutter may be a blade, a heating element, or a flexible rod having a sharpened end.

Figure 53:
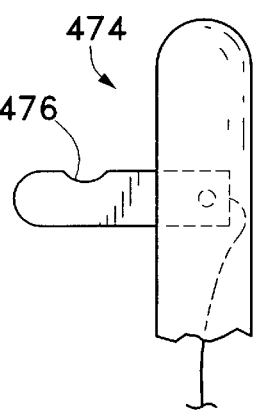

FIG. 53 illustrates a variation of a cutter 474 where the cutter 474 is a suture cutter 474 having a cutting surface 476.

FIGS. 54–60 illustrate variations of the invention described herein as used in an airway within a lung. As described above, the invention may also be attached to the exterior of the lung to compress the lung tissue from outside.

Figure 54:
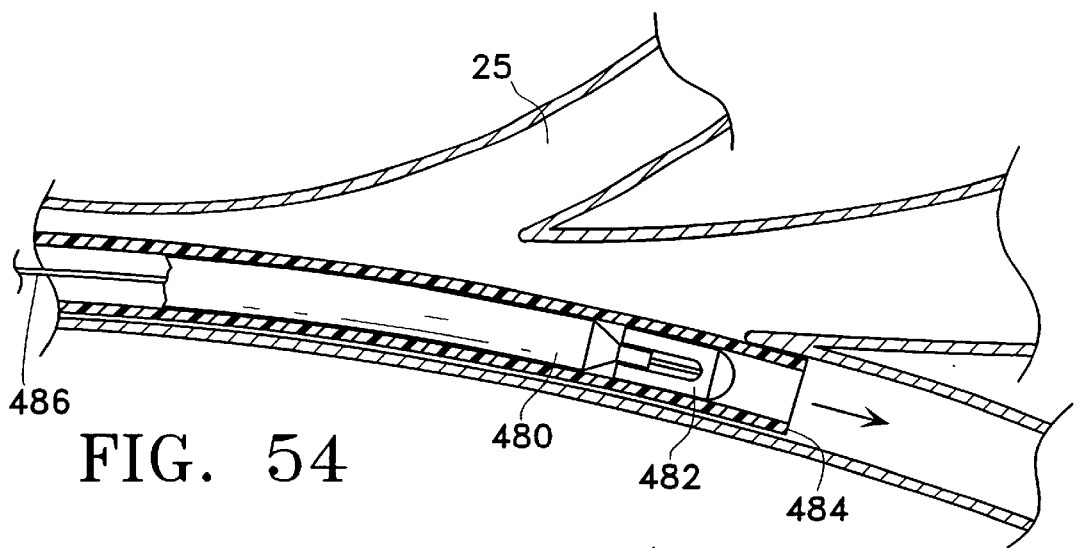
FIGS. 54–56 illustrate deployment of a variation of the present invention where an anchor is deformed by a tapered delivery device to assume an expanded profile and connected to another cord by means of a connector.

FIG. 54 illustrates a delivery device 480 having a tapered portion with an anchor 482 removably seated on an exterior of the delivery device 480. As shown, the invention may include a sheath or tube 484 to access the airway. It is understood that the invention also contemplates the use of a delivery device without a sheath or tube. For example, the delivery device 480 of FIG. 54 may be advanced into position inside an airway 25 of the lungs or to a point on the outside of the lungs without the outer tube or sheath 484. In this case, the anchor 482 will be mounted on the top of the delivery device 480 rather than inside a sheath 484.

Figure 55:
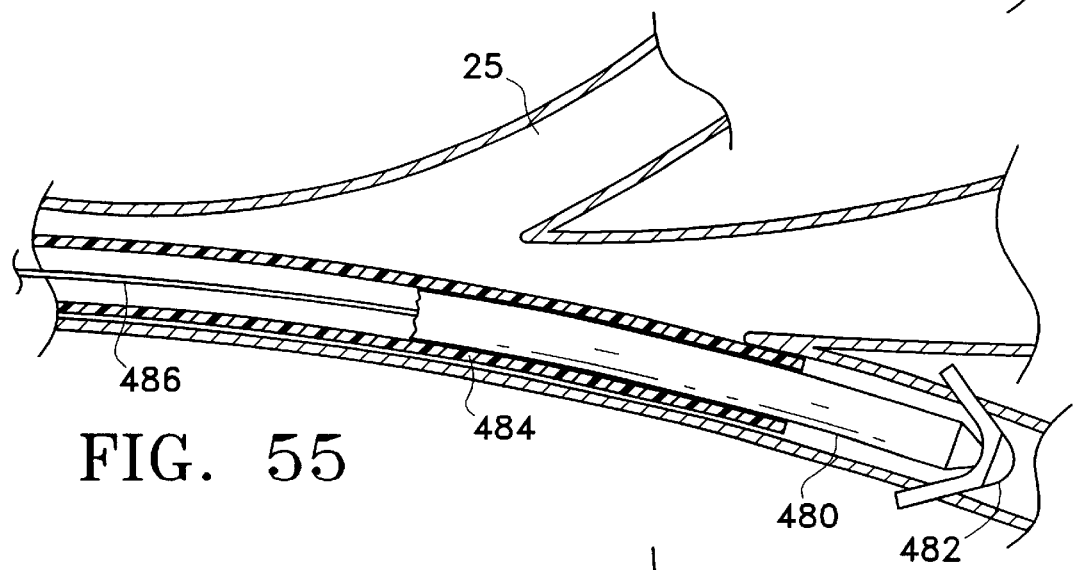

FIG. 55 illustrates the expansion of the anchor 482 as a cord 486 pulls the anchor 482 over the tapered portion of the delivery device 480. As shown, the anchor 482 attaches to the walls of the airway. As discussed above, the anchor 482 may be configured such that the anchor penetrates the airway walls or the anchor may be atraumatic and provide resistance against the walls thereby preventing movement of the anchor 482 as tension is applied to the cord 486.

Figure 56:
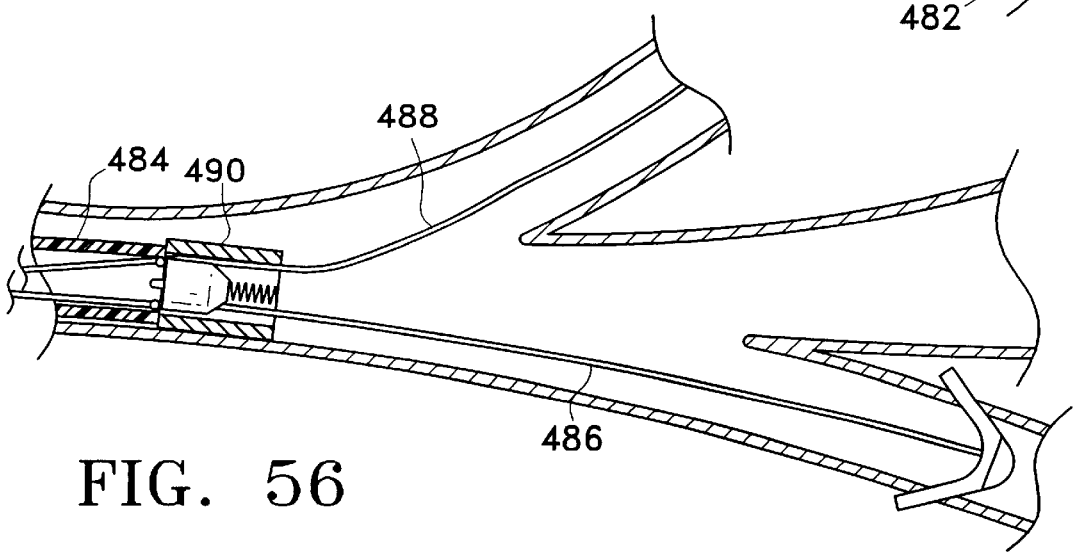

FIG. 56 illustrates the use of a connector 490 that joins multiple cords 486 and 488. It is contemplated that two anchors may be used on either end of a cord thereby eliminating the need for the connection device 490. Also, the connection device may be any of the connection devices described herein.

Figure 57:
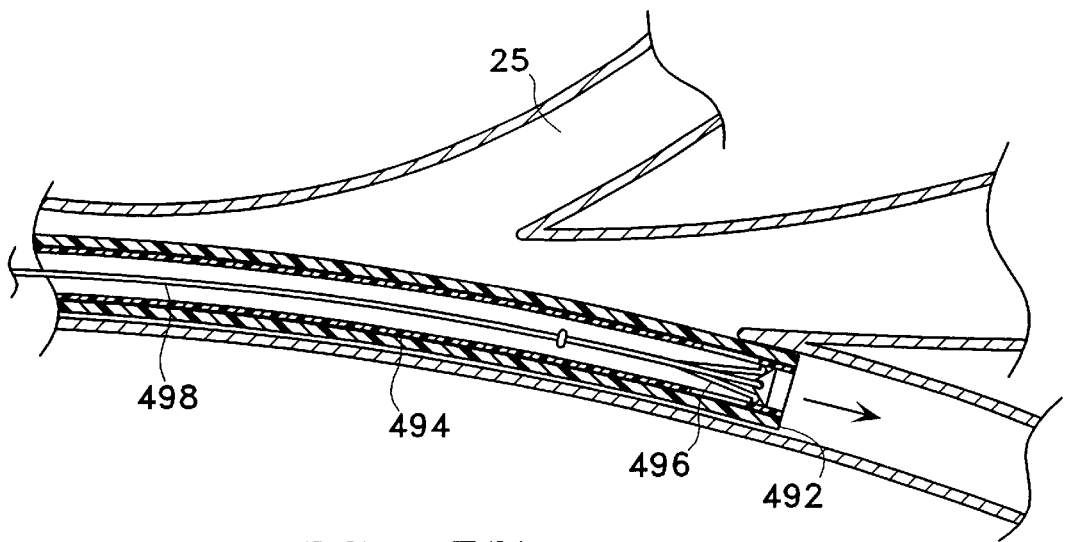
FIGS. 57–58 illustrate deployment of a variation of the present invention where an anchor is expanded by use of a wedge.
Figure 58:
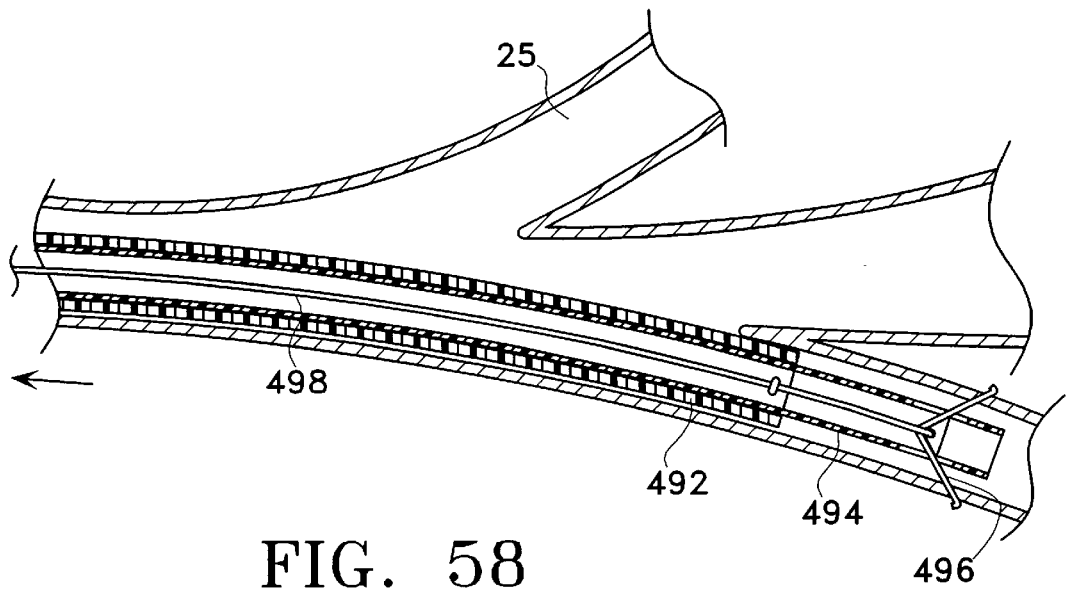

FIG. 57 illustrates another variation of the invention described herein. In this variation an anchor 496 is advanced to a target site via a delivery device 494. FIG. 58 illustrates the expansion of the anchor 496 as a cord 498 is pulled in a proximal direction causing the anchor 496 to expand.

Figure 59:
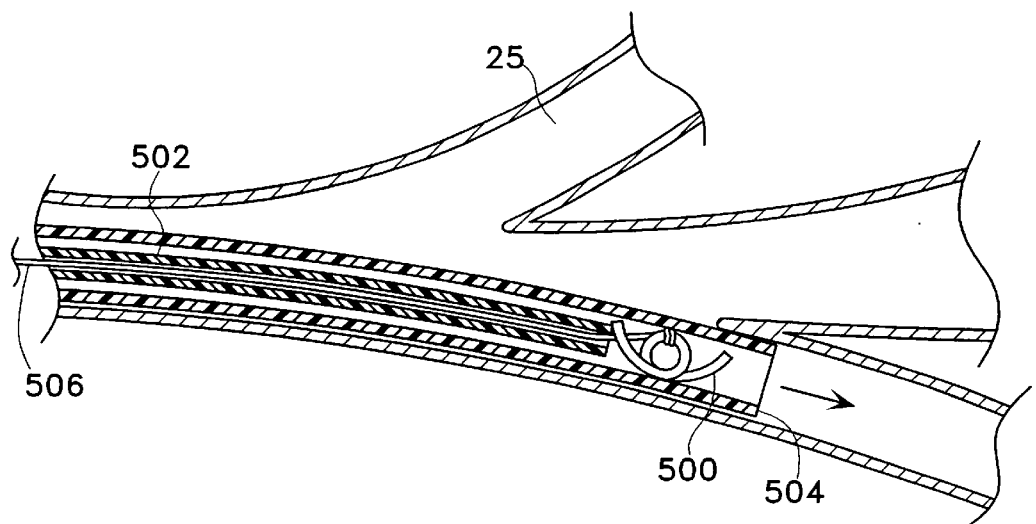
FIGS. 59–60 illustrate deployment of a variation of the present invention where an anchor is comprised of a wire and is rotated to attach to an airway wall.
Figure 60:
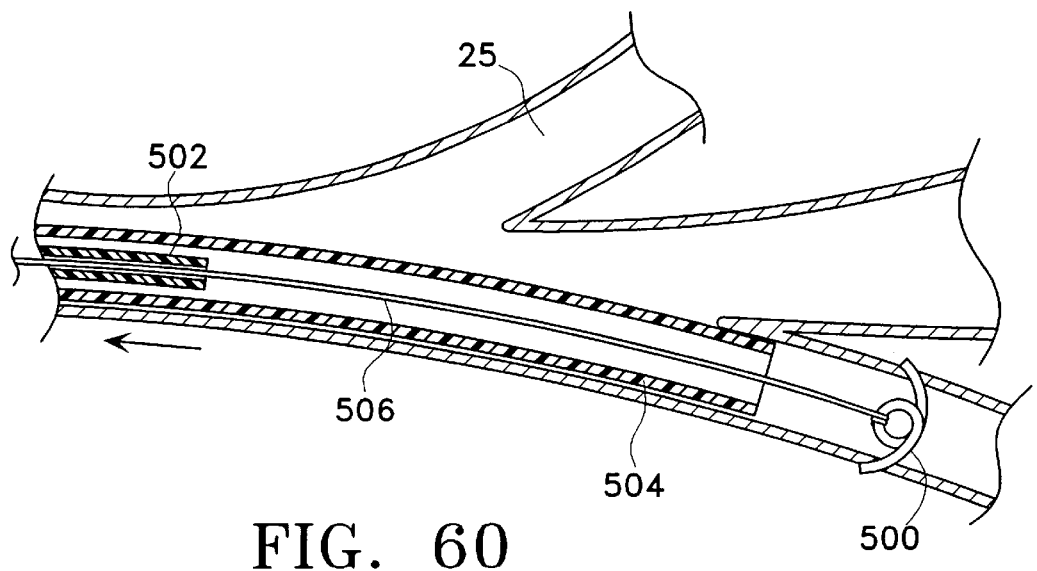

FIG. 59 illustrates another variation of the invention using a wire anchor 500. FIG. 60 illustrates advancement of the anchor 500 to the site and movement of a cord 506 in a proximal direction which rotates the anchor 500 for placement in the walls of the airway. The anchor 500 may be, for example, advanced out of the delivery device 504 by use of a push tube or wire 502. Or, the delivery device 504 along with the anchor 500 may be placed at a desired location and then the delivery device 504 may be withdrawn while the push tube or wire 502 keeps the anchor 500 at the target location. In this case, the push tube or wire 502 must be of sufficient stiffness to maintain the position of the anchor 500.

FIGS. 61A–61B illustrate a further variation of an anchor device 510. This variation of the anchor device 510 comprises a central portion 516 with attachment portions 512, 514. A cord 518 may be attached to the central portion 516 of the anchor device 510. FIG. 61A illustrates the anchor device having a reduced profile as measured by a width 520 comprising the shortest distance measured from either side of the anchor device 510. In this profile the anchor device 510 may be advanced through an airway of the lungs. FIG. 61B illustrates the anchor device 510 once rotated to assume an expanded profile as measured by a width 522. This width 522 is sufficiently larger than the width 520 such that the anchor device 510 may be anchored within the lung or with an airway within the lung. The anchor device 510 may be rotated by placing the cord 518 in tension once the anchor device 510 is deployed. The anchor device 510 illustrated in FIGS. 61A–61B is shown to have a sharpened attachment portion 512 and a blunt attachment portion 514. It is contemplated that either attachment portion may be blunt or sharpened. The configuration of the attachment portion is selected to facilitate placement of the anchor device 510 in lung or airway tissue.

FIGS. 62A–62B illustrate variations of deployment devices 524, 526 used deploy an anchor. FIG. 62A illustrates a delivery device 524 which deploys an anchor device 510 in an orientation that allows the anchor device 510 to be advanced through the lungs to a target site. FIG. 62B illustrates another device 526 which deploys an anchor device 510 in a significantly reduced profile.

FIG. 63 illustrates a possible deployment position of the anchor device 510 of FIGS. 61A–61B. As mentioned above, the anchor device 510 may have an attachment portion 512 that punctures a wall of the airway or other lung tissue and an attachment portion 514 that is relatively atraumatic to lung tissue. Again, as mentioned above, the anchor device may be configured such that both attachment portions are either sharpened or blunt.

Figure 64:
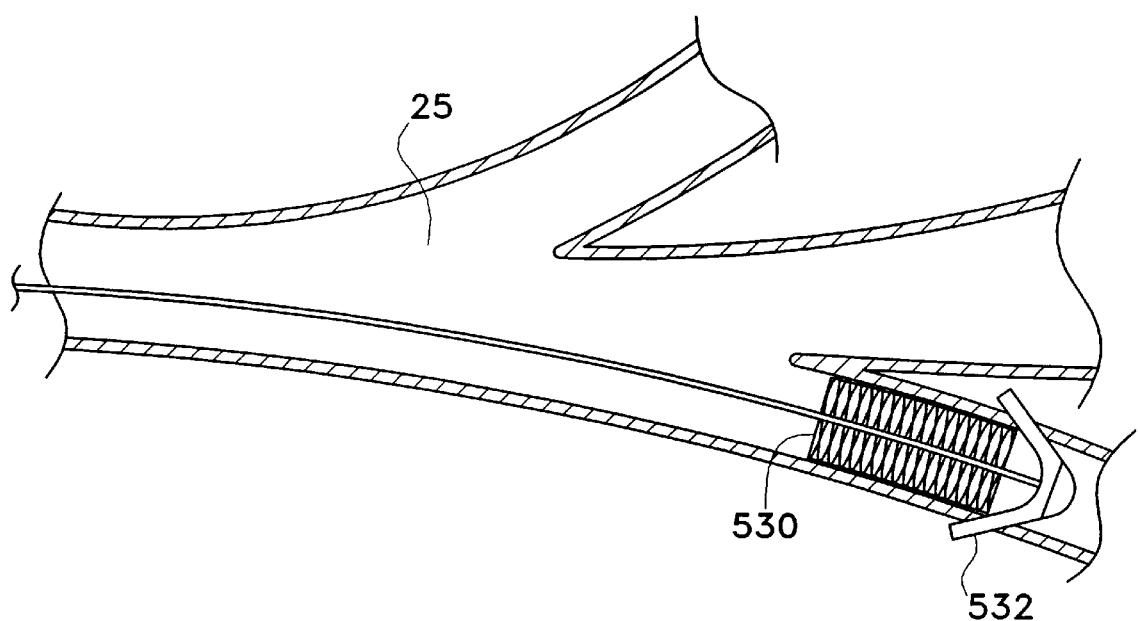
FIG. 64 illustrates a support member placed within a lung to increase the anchoring ability of an anchor.

FIG. 64 illustrates another variation of the invention where a support member 530 is placed within the lung, for example, an airway of the lung. The support member 530 creates an area of improved anchor support for increasing the anchoring ability of any of the anchors described herein. The support member 530 may be placed within the lung in an area that is intended to be compressed prior to placement of the anchor. The support member 510 may then be left in the lung for a period of time to allow fibrosis of tissue over the support member 530 to assist in retaining the support member 530 within the lung. The support member may also be used with a tissue irritant or fibrosing agent as described herein or any other substance that facilitates placement of the support member 530 at a desired location. The support member 530 may be constructed of a mesh, woven, or solid design. The support member 530 may be expandable or a tube or any other design that facilitates placement within the lung. Also, although FIG. 64 depicts the support member 530 as a tubular structure, it may be of another shape such as a ring or other non-circular shape.

The invention further includes the method of minimally invasively or non-invasively treating a lung having at least an emphysematous portion comprising the step of improving a pulmonary function of at least a first portion of the lung.

The step of improving a pulmonary function may comprise reducing hyperinflation of a second portion of the lung, increasing the range of motion of the diaphragm, redirecting airflow to a healthier portion of the lung, and/or reducing a volume of a second portion of the lung to remove non-functional residual air from the lung.

The step of improving a pulmonary function may comprise attaching a first anchor to the lung, attaching a second anchor to the lung, connecting a cord between the second anchor and the first anchor, and shortening the length of the cord between the first and second anchors to compress a second portion of the lung. The method may include the use of a connector to join the first and second anchors.

The method of improving a pulmonary function may also include the step of deflating the lung or the diseased portion of the lung prior to the shortening step. Deflating the lung may allow a more controlled adjustment of the connections between the lines and connecting device since less force will be exerted by the expanded lung section.

The method of improving a pulmonary function may also include injecting a sclerosant agent into the second portion of the lung to maintain compression of the second portion. An example of a sclerosant agent is powdered talc or a slurry composed of powdered talc and water or saline. However, sclerosant agents can be composed of any biocompatible agent that also produces a degree of tissue irritation. Currently, a common use of sclerosant agents is to encourage the formation of adhesions between the outer wall of the pleura and the chest cavity during lung surgery. Likewise, it is anticipated that sclerosant agents will form adhesions between the inner walls of the diseased portion of lung that has been compressed by the invention disclosed herein, further encouraging the compressed section to remain compressed over time.

The invention also includes a lung volume reduction apparatus kit comprising at least one anchor having a reduced profile and configured to assume an expanded profile wherein in the expanded profile the anchor secures to the lung and in the reduced profile the anchor is capable of being advanced in an airway of a lung, at least one connector, at least one cord having a proximal end and a distal end, the proximal end being attached to at least one of the connectors and the distal end being attached to at least one of the anchors, and a delivery device being configured to removably nest at least one of the anchors on a distal end.

The invention further includes a kit comprising the apparatus previously described and a bronchoscope. The kit may also include a fibrosing and/or sclerosant agent.

The invention further includes the step of preparing the lung volume reduction apparatus described above for use in a medical procedure comprising the steps of sterilizing the lung volume reduction apparatus and packaging the lung volume reduction apparatus.

The invention also includes a modified lung having an artificially compressed portion being compressed by at least two anchors secured in at least two discrete attachment areas of the lung and joined by at least one cord, wherein the anchors compress the area between the discrete attachment areas.

The invention also includes the method of teaching the use of any of the devices or methods described herein.

The network of alveoli in lungs provides strength to the airway walls, as well as elasticity to the lungs, both of which contribute to the lung's ability to function effectively. In cases of severe chronic pulmonary disease, such as emphysema, lung tissue is destroyed, reducing the strength of the airways. This reduction and strength of the airway walls allows the walls to become "floppy" thereby losing their ability to remain open during exhalation. In this diseased state, the patient suffers from the inability to get the air out of their lungs due to the collapse of the airways during exhalation. Heavily diseased areas of the lung become overinflated. Within the confines of the chest cavity, this overinflation restricts the in-flow of fresh air and the proper function of healthier tissue, resulting in significant breathlessness.

The present invention strives to address the above problems of overinflated and inefficient lung tissue in patients by compressing the volume of a severely diseased area of the lung, allowing the remaining healthier tissue to function more efficiently and improve patient breathing. Because the diseased portion of the lung has been collapsed or compressed, the remaining healthy tissue is redistributed, improving air exchange. According to one embodiment of the present invention, a plurality of anchors are lodged in the lung near the most distal part of the bronchial passageways of the lung. The anchors are drawn towards one another to cause the lung to collapse, thus compressing the airflow tissue in the lung and establishing a permanent reduction in lung volume. All of this is accomplished by a technique that is not nearly as invasive as prior art techniques for addressing this problem. The technique performed by the present invention can be performed without making a single incision. Accordingly, the risk of serious post-operative complications is greatly reduced.

The principles, preferred embodiments and modes of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims be embraced thereby.

What is claimed is:

1. A lung volume reduction device comprising:
   a) at least one anchor having a reduced profile and being configured to assume an expanded profile wherein in said reduced profile said anchor is capable of being advanced into an airway of the lung and in said expanded profile said anchor secures to lung tissue;
   b) at least one connector;
   c) at least one cord having a proximal end and a distal end, said proximal end being attached to at least one of said connectors which is adapted to be self-locking about said cord and said distal end being attached to at least one of said anchors; and
   d) a delivery device being configured to removably seat at least one of said anchors on a distal end.

2. The lung volume reduction device of claim 1, wherein said connector comprises:
   a) a body having at least one passageway sized to permit passage of the cord; and
   b) a stop having at least a portion connected to each of said passageways said stop configured to prevent movement of the cord after the cord is fed through said passageway to a desired location.

3. The lung volume reduction device of claim 2 wherein said body is plastically deformable such that deformation of said body reduces a diameter of said passageway to create said stop.

4. The lung volume reduction device of claim 2 wherein said stop comprises at least one tapered plug having a first and second diameters and at least one ring having an inner diameter sized between said first and second diameters of said plug, said ring located co-axially with each of said passageways, wherein movement of the at least one cord may be prevented by passing the at least one cord through said ring and inserting said tapered plug into said ring.

5. The lung volume reduction device of claim 2 wherein said connector further comprises a tube slidably located within said passageway, said tube having a lumen sized to permit passage of the at least one cord, and wherein said stop comprises a plurality of stops, wherein upon removal of said tube from said passageway causes said stops to frictionally hold the cord.

6. The lung volume reduction device of claim 2 wherein said stop comprises a moveable section within said body, said moveable section having a hole sized to permit passage of the cord, said moveable section having an aligned position such that said hole is in alignment with said passageway which allows movement of the cord, and a non-aligned position such that said hole is not in alignment with said passageway which prevents movement of the cord.

7. The lung volume reduction device of claim 6 wherein said moveable section is biased to assume said non-aligned position.

8. The lung volume reduction device of claim 6 wherein said moveable section is retained in said aligned position by a removable tube extending through said passageway and said hole.

9. The lung volume reduction device of claim 2 wherein said stop comprises a section of reduced diameter in said passageway.

10. The lung volume reduction device of claim 9 further comprising a flange within said passageway, said flange having a plurality of slots radially extending from a central opening, wherein said center opening comprises said section of reduced diameter and is sized to permit movement of the cord and said slots are sized to prevent movement of the cord.

11. The lung volume reduction device of claim 9 wherein said stop further comprises a plug which seats in said section of reduced diameter to provide frictional resistance against the cord to prevent movement of the cord.

12. The lung volume reduction device of claim 11 wherein said plug is directionally biased towards said section of reduced diameter by a spring.

13. The lung volume reduction device of claim 11 wherein said plug comprises a spherical stop.

14. The lung volume reduction device of claim 13 wherein said connector comprises six passageways and said stop comprises six spherical stops.

15. The lung volume reduction device of claim 2 wherein said passageway further comprises a plurality of prongs extending away from said body towards a center of said passageway, said prongs configured to retain the proximal end of the cord or to interfere with the cord and hold it in place by frictional forces.

16. The lung volume reduction device of claim 2 for use with the lung reduction device additionally having a cord with a segment of increased diameter, wherein said stop of said connector comprises a stopper slidably located within said passageway and attached to said body by a spring element such that said stopper maintained in said passageway and is temporarily moveable out of a proximal end of said body, said stopper having a proximal diameter less than a diameter of said passageway, wherein after the segment of increased diameter of the cord is pulled from a distal end of said body through said proximal end of said body and past said stopper, said stopper prevents substantial movement of the cord in a distal direction.

17. The lung volume reduction device of claim 16 wherein a base of said distal end of said body comprises said spring element.

18. The lung volume reduction device of claim 16 wherein said stopper has a plug extending out of said proximal end of said body, wherein said plug is configured allow said stopper to be temporarily pulled out of said passageway to release the cord.

19. An anchor for use with a lung volume reduction device having a connector joining said anchor to a second anchor, wherein said anchor comprises:
   a central portion and an attachment portion connected to said central portion, said attachment portion being moveable between a reduced profile and an expanded profile, wherein when in said reduced profile said anchor is capable of being advanced into a passageway of the lung and when in said expanded profile said attachment portion attaches to lung tissue; and
   at least one cord having a distal end and a proximal end, said distal end being attached to said central portion of said anchor and said proximal end secured to the connector which is adapted to be self-locking about said cord.

20. The anchor of claim 19 wherein said central portion comprises a wire having at least one loop, and said attachment portion comprises a first end and second end of said wire, where rotation of said anchor in the lung passageway permits said ends of said wire to contact the lung causing said anchor to assume said expanded profile.

21. The anchor of claim 19 wherein said anchor comprises a segment having a first and second end, wherein said central portion of said anchor is located between said first and second ends, said first end is configured to be atraumatic and said second end is configured to penetrate lung tissue, wherein rotation of said anchor in the lung passageway permits said ends to contact lung tissue causing said anchor to assume said expanded profile.

22. The anchor of claim 19 wherein said anchor comprises a flat spring, said ends of said spring comprising said attachment portion, said spring folded about a center point, said fold forming said central portion of said anchor, said spring further comprising barbs along a surface of said spring.

23. The anchor of claim 19 wherein said attachment portion comprises at least one tine, each said tine having a first end and a second end, said first end being attached to said central portion, wherein when said second ends of said tine move away from said central portion said anchor assumes said expanded profile.

24. The anchor of claim 23 further comprising a fibrosing agent on at least a surface of said anchor.

25. The anchor of claim 24 wherein said fibrosing agent is located adjacent to said tine of said anchor.

26. The anchor of claim 23 wherein each of said attachment portion is sized to enter an airway of less than 3 mm in approximate diameter.

27. The anchor of claim 23 wherein said attachment portion comprises three tines.

28. The anchor of claim 23 wherein said attachment portion comprises four tines.

29. The anchor of claim 23 wherein said second end of each said tine is configured to prevent movement of the anchor relative to the airway when said anchor is in said expanded profile.

30. The anchor of claim 23 wherein said anchor is configured to be atraumatic to the lung.

31. The anchor of claim 23 wherein each said tine is plastically deformable such that said anchor retains said expanded profile upon deformation of said tine.

32. The anchor of claim 23 wherein said anchor is mechanically deformable to assume said expanded profile.

33. The anchor of claim 23 wherein at least said tines comprises a shape-memory alloy and said anchor is thermally deformable to assume said expanded profile.

34. The anchor of claim 23 wherein said anchor is spring biased to assume said expanded profile.

35. The anchor of claim 23 wherein said cord further comprises a wedge attached to a distal end of said cord, said at least one tine comprises at least two of said tines, and said wedge being slidably attached to said anchor between at least two of said tines, when said wedge is proximate to said second end of said tines said anchor is in said reduced profile, and when said wedge slides towards said central portion of said anchor, said wedge displaces said tines so that said anchor assumes said expanded profile.

36. The anchor of claim 35 wherein said anchor further comprises at least one stop attached to at least one of said tines to fixedly attach said wedge adjacent to said central portion.

37. The anchor of claim 23 wherein said anchor further comprises at least one covering having a wall, said wall having a plurality of openings, said covering being placed over said central portion, said second end of said tine extending through said openings of said covering, wherein movement of said central portion within said covering advances or retracts said second end of said tine through said openings.

38. The anchor of claim 23 wherein said cord further includes a hook attached to said proximal end of said cord.

39. The anchor of claim 23 wherein said cord is elastic.

40. The anchor of claim 39 wherein said cord comprises a tube having a lumen.

41. The anchor of claim 23 wherein said cord comprises at least two segments each having different diameters.

42. The anchor of claim 41 wherein at least one of said segments comprises a ball-bearing fixedly attached to said cord.

43. A delivery device for use with a lung volume reduction device, wherein said delivery device comprises:

an elongate member having a distal and a proximal end, said elongate member being adapted to be advanced within airways of at least one lung, said elongated member being configured to removably seat the anchor on a distal end of the elongated member wherein said lung volume reduction device has at least one cord having a proximal end and a distal end, the distal end of the cord being attached to said anchor and the proximal end of the cord being attached to at least one connector which is adapted to be self-locking bout said cord.

44. The delivery device of claim 43 wherein said elongated member further comprises a fluid delivery port at a proximal end of said elongated member, a lumen extending between said proximal and distal ends of said elongated member, and a seal in said lumen at said proximal end, said seal configured to allow the cord to exit from said proximal end while keeping said lumen fluidly sealed at said proximal end.

45. The delivery device of claim 43 wherein at least said distal end of said elongated member is hollow and sized to seat the anchor.

46. The delivery device of claim 45 wherein said elongated member has at least two slots located at said distal end, each said slot being sized to allow a portion of the anchor to expand through said slot.

47. The delivery device of claim 43 wherein said distal end of said elongated member further comprises a tapered section, said distal end being configured so that retracting the anchor in a proximal direction over said tapered section causes the anchor to expand to assume the expanded profile.

48. The delivery device of claim 43 wherein said distal end comprises a compressible sleeve located between the anchor and the elongate member, compressing said sleeve in a lengthwise direction causes said sleeve to expand to an increased diameter, expansion of said sleeve to said increased diameter mechanically deforms the anchor to assume the expanded profile.

49. The delivery device of claim 43 further comprising a cutter configured to sever the cord.

50. The delivery device of claim 49 wherein said cutter is a suture cutter.

51. The delivery device of claim 49 wherein said cutter is a blade within said elongate member.

52. The delivery device of claim 49 wherein said cutter is a flexible rod having a sharpened end for cutting the cord.

53. The delivery device of claim 49 wherein said cutter comprises a first shearing surface and a second shearing surface.

54. The delivery device of claim 53 wherein said elongate member comprises said first shearing surface, and said second shearing surface is moveable within said elongate member such that the section of the cord between said first and second shearing surfaces is cut as said first and second shearing surfaces join.

55. The delivery device of claim 54 wherein said second shearing surface is configured to move at least axially within said elongate member.

56. The delivery device of claim 54 wherein said second shearing surface is configured to move at least torsionally within said elongate member.

57. The delivery device of claim 49 wherein said cutter comprises a heating element configured to melt the cord.

58. A method for minimally invasively or non-invasively treating a lung having at least an emphysematous portion comprising the step of improving a pulmonary function of at least a first portion of the lung by reducing a volume of a second portion of the lung while maintaining communication between the first portion and the second portion.

59. The method of claim 58 wherein the step of improving a pulmonary function of at least the first portion of the lung comprises reducing hyperinflation of the second portion of the lung.

60. The method of claim 58 wherein the step of improving a pulmonary function of at least the first portion of the lung comprises increasing the range of motion of the diaphragm.

61. The method of claim 58 wherein the step of improving a pulmonary function of at least the first portion of the lung comprises redirecting airflow to a healthier portion of the lung.

62. The method of claim 58 wherein the step of reducing the volume of the second portion of the lung comprises removing non-functional residual air from the lung.

63. The method of claim 58 wherein the step of improving a pulmonary function of at least the first portion of the lung comprises the steps of attaching a first anchor to the lung;

attaching a second anchor to lung, connecting a cord between the second anchor and the first anchor; and shortening the length of the cord between the first and second anchors to compress the second portion of the lung.

64. The method of claim 63 further comprising the step of deflating at least a portion of the lung prior to said shortening step.

65. The method of claim 63 further comprising the step of injecting a sclerosant agent in the second portion of the lung to maintain the compression of the second portion.

66. The method of claim 63 wherein the first anchor and the second anchor each have separate cords, and said connecting step uses a connector to connect the cords of each anchor.

67. The method of claim 63 further comprising the step of placing at least one support member in the lung to create an area of improved anchor support for increasing the anchoring ability of at least one of the anchors.

68. A lung volume reduction device kit comprising:

a) the lung volume reduction device of claim 1; and b) a bronchoscope.

69. The lung volume reduction device kit of claim 68 further comprising a fibrosing agent.

70. The lung volume reduction kit of claim 68 further comprising a sclerosant.

71. The lung volume reduction device kit of claim 68 in which each instrument in the kit has been rendered sterile and been packaged to maintain sterility of the instruments.

72. A method for preparing the lung volume reduction device of claim 1 for use in a medical procedure comprising the steps of:

sterilizing the lung volume reduction device; and packaging the lung volume reduction device.

* * * * *